US009990864B2

(12) United States Patent
Senanayake et al.

(10) Patent No.: US 9,990,864 B2
(45) Date of Patent: Jun. 5, 2018

(54) MONITORING OF A TIME PERIOD RELATING TO A PRODUCT

(71) Applicant: Senver Pty Ltd, Sutherland, North South Wales (AU)

(72) Inventors: Sanjaya Naresh Senanayake, Sutherland (AU); Gary Martin Verdickt, Sutherland (AU); Dilukshi Tarindu Senanayake, Sutherland (AU); Kushlani Kumari Verdickt, Sutherland (AU); Luke Thomas Dawson, Sutherland (AU); Stuart Richard May, Sutherland (AU)

(73) Assignee: Senver Pty Ltd (AU)

( * ) Notice: Subject to any disclaimer, the term of this patent is extended or adjusted under 35 U.S.C. 154(b) by 0 days. days.

(21) Appl. No.: 15/363,417

(22) Filed: Nov. 29, 2016

(65) Prior Publication Data

US 2017/0076641 A1  Mar. 16, 2017

Related U.S. Application Data

(63) Continuation-in-part of application No. PCT/AU2015/050277, filed on May 26, 2015.

(30) Foreign Application Priority Data

May 29, 2014 (AU) ................................ 2014902045
Oct. 2, 2014 (AU) ................................ 2014903936

(51) Int. Cl.
*G08B 13/02* (2006.01)
*G09F 3/00* (2006.01)
(Continued)

(52) U.S. Cl.
CPC .............. *G09F 3/0288* (2013.01); *A61B 5/00* (2013.01); *A61B 90/90* (2016.02); *A61M 25/002* (2013.01);
(Continued)

(58) Field of Classification Search
CPC combination set(s) only.
See application file for complete search history.

(56) References Cited

U.S. PATENT DOCUMENTS 5,802,015 A * 9/1998 Rothschild .............. G04F 1/005
116/202
8,068,011 B1 * 11/2011 Sajadi ................. H04M 1/7253
340/10.4
(Continued)

FOREIGN PATENT DOCUMENTS

WO  2000073859 A1  12/2000
WO  2011038045 A2  3/2011
(Continued)

OTHER PUBLICATIONS

International Search Report and Written Opinion for Application No. PCT/AU2015/050277 dated Aug. 7, 2015.
(Continued)

*Primary Examiner* — Brian Zimmerman
*Assistant Examiner* — Cal Eustaquio
(74) *Attorney, Agent, or Firm* — Lerner, David, Littenberg, Krumholz & Mentlik, LLP

(57) ABSTRACT

A label includes a timer to monitor a predetermined time period relating to a medical device, such as an indwelling cannula, or other product. The label includes a signalling apparatus that provides an alert signal on expiry of the predetermined time period and a fixing portion to fix the label to a support surface such as medical records of a patient. The label can have a first portion and a second portion and the first portion can be separable from the second portion. The fixing portion can be provided in the second portion and all or part of the signalling apparatus provided in the first portion. Also disclosed is a monitoring system for a medical device, including a base station and a
(Continued)

label receivable by the base station. The monitoring system monitors a predetermined time period based on receipt of the label by the base station.

20 Claims, 15 Drawing Sheets

(51) Int. Cl.
*A61B 5/00* (2006.01)
*G06Q 50/24* (2012.01)
*G07C 1/00* (2006.01)
*G09F 1/00* (2006.01)
*G06F 19/00* (2018.01)
*A61B 90/90* (2016.01)
*G04C 21/00* (2006.01)
*G04F 1/00* (2006.01)
*G04F 3/06* (2006.01)
*A61M 25/00* (2006.01)
*G08B 21/18* (2006.01)
*G09F 3/10* (2006.01)
*G09F 27/00* (2006.01)
*G09F 3/02* (2006.01)

(52) U.S. Cl.
CPC ......... *A61M 25/0017* (2013.01); *G04C 21/00* (2013.01); *G04F 1/005* (2013.01); *G04F 3/06* (2013.01); *G06F 19/323* (2013.01); *G06Q 50/24* (2013.01); *G07C 1/00* (2013.01); *G08B 21/18* (2013.01); *G09F 1/00* (2013.01); *G09F 3/10* (2013.01); *G09F 27/004* (2013.01); *A61B 2560/028* (2013.01); *A61M 2205/82* (2013.01); *G09F 2003/0272* (2013.01)

(56) References Cited

U.S. PATENT DOCUMENTS

| | | |
|---|---|---|
| 2003/0160098 A1 | 8/2003 | Humbert et al. |
| 2006/0187003 A1 | 8/2006 | Terenna |
| 2007/0064541 A1 | 3/2007 | Kagan |
| 2009/0209896 A1 | 8/2009 | Selevan |
| 2010/0049888 A1 | 2/2010 | Zhang et al. |
| 2011/0071482 A1 | 3/2011 | Selevan |

FOREIGN PATENT DOCUMENTS

| | | |
|---|---|---|
| WO | 2011044256 A1 | 4/2011 |
| WO | 2014100906 A1 | 7/2014 |

OTHER PUBLICATIONS

Extended European Search Report for EP15799809 dated Feb. 1, 2018.

* cited by examiner

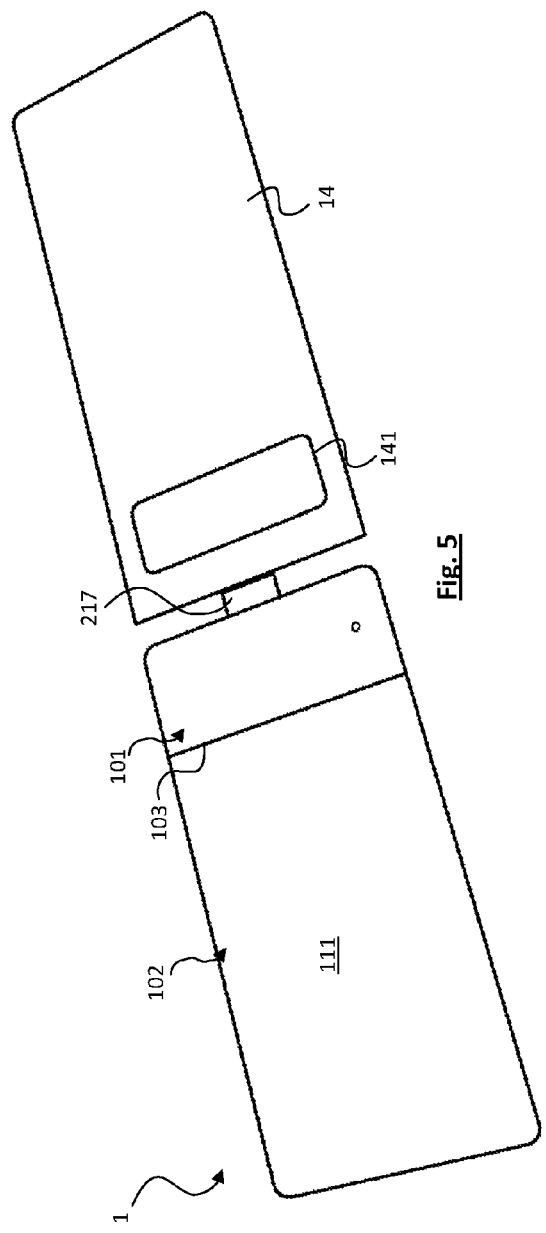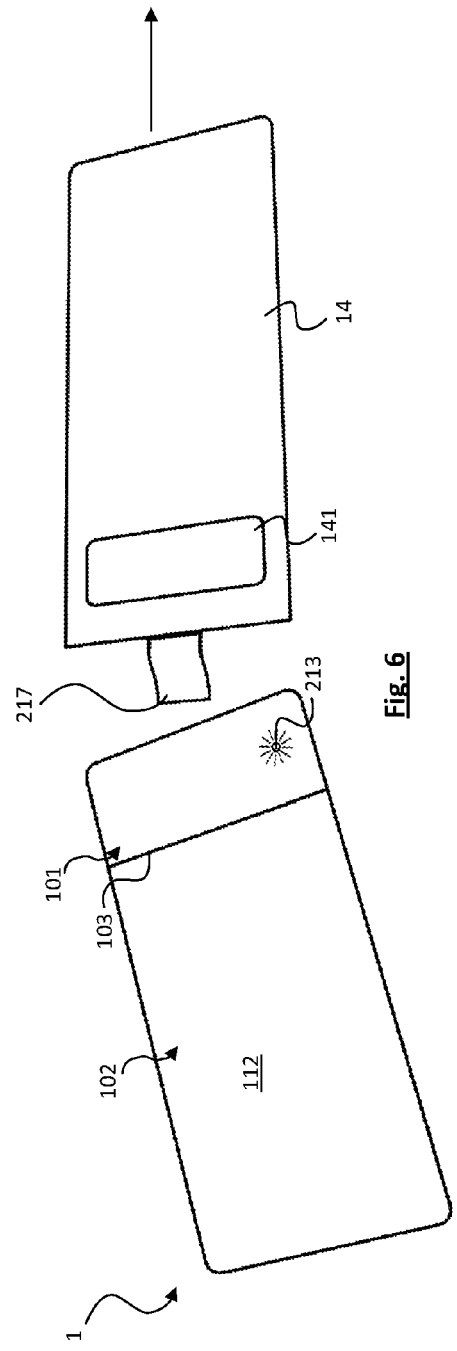

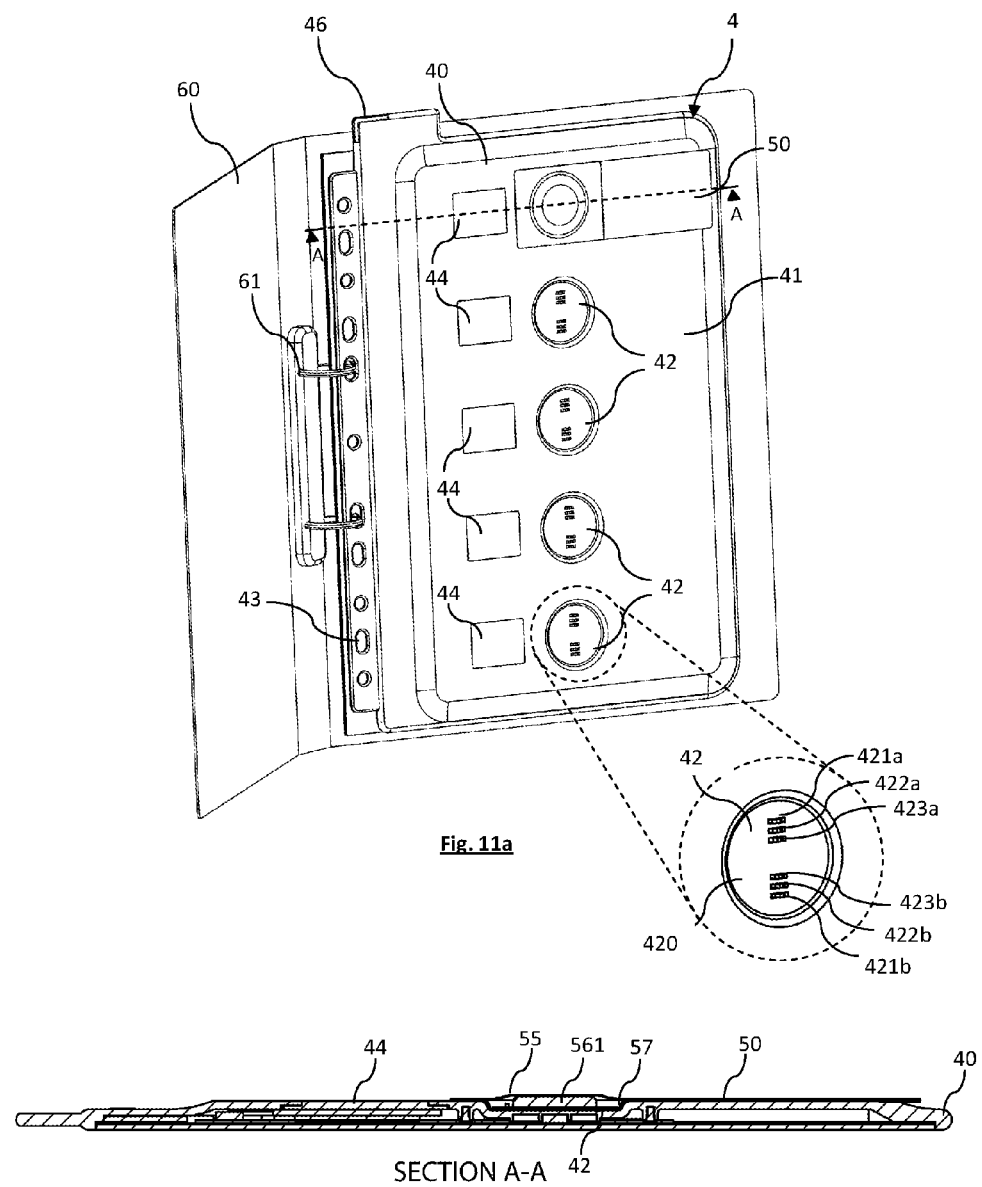

MONITORING OF A TIME PERIOD RELATING TO A PRODUCT

CROSS-REFERENCE TO RELATED APPLICATIONS

The present application is a continuation-in-part of International Application No. PCT/AU2015/050277, filed on May 26, 2015, which claims priority to Australian Provisional Patent Application No. 2014902045, filed on May, 29 2014, and Australian Provisional Patent Application No. 2014903936, filed on Oct. 2, 2014, the disclosures all of which are incorporated herein by reference.

TECHNICAL FIELD

The present disclosure pertains to monitoring of a time period relating to a product, e.g., a medical product such as a medical device or a pharmaceutical, in order, for example, to reduce the risk of a patient contracting an infection or suffering other harm through prolonged use of the product.

BACKGROUND

Despite stringent hospital guidelines for controlling the spread of bacteria, hospital-acquired infections, also known as healthcare-associated infections or "HAIs", are commonplace. HAIs result in unnecessary suffering for patients, extended healthcare and hospital times and significant costs to healthcare systems.

A significant proportion of HAIs are caused through use of indwelling medical devices that are inserted in patients for longer than a safe time period. For example, an intravenous cannula can be inserted in a patient's vein to deliver fluids, drugs or medical instruments. However, the intravenous cannula can also act as a conduit for bacteria to enter the human body and can provide a protected environment for bacterial incubation, leading to HAIs. With approximately 1.5 billion cannulae implanted in patients globally each year, reducing the number of HAIs caused by cannulae and other medical devices, such as urethral catheters, is paramount.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to an aspect of the present disclosure, there is provided a label comprising:
a timer to monitor a predetermined time period relating to a product;
a signalling apparatus that provides an alert signal on expiry of the predetermined time period; and
a fixing portion to fix the label to a support surface.

The product may be a medical device or other type of product. The label may be considered a medical label or medical device label, for example. In one embodiment, the support surface is provided by medical records of a patient. In another embodiment, the support surface is provided by a container.

The medical device, relating to which the predetermined time period may be monitored, may be a device that is at least partially inserted in or placed on a patient for a period of time. For example, the medical device may be an indwelling medical device, such as an invasive conduit or cannula. Example medical devices include intravenous cannulae and urethral catheters. The medical device may be located in a patient intravenously, intravascularly, intra-arterially, intracranially, intra-urethrally or otherwise. The predetermined time period may be a maximum period that is considered safe for indwelling of the medical device. The predetermined time period may be based on pre-existing medical standards, protocols or regulations. Upon expiry of the predetermined time period, it may be understood that the risk of the patient developing an infection (e.g., an HAI) is increased to an unacceptable level.

The medical device is not necessarily an invasive device or a device that may increase risk of infection, however. The medical device may be any medical device for which monitoring of a predetermined time period is desired. For example, the medical device may be a compression bandage that should be removed within a specific period of time, or a drug delivery patch that should be removed within a specific period of time. As another example, the medical device may be a hospital bed, wherein a patient lying on the bed should be encouraged to move periodically to avoid pressure sores.

By providing a label that includes a timer to monitor the predetermined time period, the label can provide an indication to a user, such as a nurse, clinician or other medical practitioner, or in some instances to the patient themselves, that a particular action needs to be taken in relation to the medical device or other product. The alert signal provided on expiry of the predetermined time period may indicate to the user that the particular action needs to be taken. The action that needs to be taken may be removing or replacing the medical device or other product, checking of the patient using the medical device or other product, checking functioning of the medical device or other product, reviewing whether or not the device or other product should remain in place and, if so, when it should next be reviewed, ceasing use of the medical device or other product or otherwise.

As indicated, in one embodiment the support surface to which the fixing portion is fixed may be provided by medical records of a patient. By configuring the label to be fixed to medical records, the label may be readily accessible by the user, and held in a secure location at least during the duration of monitoring of the predetermined time period. In general, a patient's medical records may remain in close proximity to the patient at all times, e.g., through location in a records holder (usually at the end of the patient's bed), and medical records are therefore readily and regularly accessible by medical staff. A patient's medical records are a source of status information relating to the patient, and therefore an ideal location for the label. This contrasts, for example, with placement of a monitoring system such as a timer on medical device(s) attached to the patient, or placement directly on the patient. In these circumstances, the monitoring system may be more prone to damage or interference, or may be more likely to cause damage or interference to other equipment. For example, should the patient need to undergo a MRI scan, it may be necessary to remove any monitoring system placed on the patient, or on medical devices attached to the patient, to avoid interference with MRI apparatus. Further, when the monitoring system is placed on another medical device (e.g., an adhesive dressing or cannula line, etc.) that medical device may need to be replaced before the predetermined time period being monitored has ended, and before it is desirable to end monitoring of the predetermined time period.

The medical records may comprise one or more sheet elements, e.g. sheets of paper, plastic or card. The medical records may comprise a board, file or folder. The fixing portion may be planar to enable fixation to a planar surface of the medical records.

The entire label or a part thereof may be designed for disposal after expiry of the predetermined time period. The label may be a single-use label.

The label may be associated with a specific medical device. The label may be associated with a medical device by being packaged and/or attached to the medical device prior to use. Additionally or alternatively, the label may be associated with a medical device by being labelled as specifically for use with the medical device, or labelled as appropriate for use with that type of medical device, e.g., by virtue of information displayed on the label and/or on documentation or packaging accompanying the label. Additionally or alternatively, the label may be associated with a medical device by being configured to monitor a predetermined time period that is known to be relevant to that type of medical device.

In some embodiments, the product relating to which the predetermined time period is monitored may be a substance or material that has a specific expiry period or recommended usage period. For example, the product may be an ingestible substance, a pharmaceutical, a biologically active agent, a monoclonal antibody, a disinfectant, a foodstuff and/or any other substance or material that has a specific expiry or usage period. When the product is a pharmaceutical, the pharmaceutical may be an antibiotic, probiotic, steroid, anaesthetic, antidepressant or any other type of pharmaceutical. The pharmaceutical may be presented in the form of a fluid, tablet, capsule, powder or otherwise.

The product may be held in a container and the specific expiry or usage period may be initiated by opening of the container and/or breaking of a seal of the container. The container may be a sealed container that, once opened, should be discarded, or at least have its contents discarded, after the specific expiry or usage period has ended. The predetermined time period monitored by the timer of the label may correspond exactly to or closely to the specific expiry or usage period. The container may be a bottle, packet, box, can, sachet or carton, for example.

When the product relating to which the predetermined time period is monitored is held in a container, the support surface to which the label is to be fixed may be part of the container. The support surface may be an outer surface of the container, for example, so that the label, when fixed to the support surface, is easily visible to a user.

In any aspect or embodiment described herein, the label may comprise a first portion and a second portion. In some embodiments, the first portion is separable from the second portion. All or part of the fixing portion may be comprised in the second portion and all or part of the signalling apparatus may be comprised in the first portion.

According to one aspect of the present disclosure, there is provided a label comprising:

a timer to monitor a predetermined time period relating to a product;

a signalling apparatus that provides an alert signal on expiry of the predetermined time period; and a fixing portion to fix the label to a support surface, wherein the label comprises a first portion and a second portion, the first portion located towards a first end of the label and a second portion located towards a second end of the label opposite to the first end, and wherein the signalling apparatus is comprised in the first portion and the fixing portion is comprised in the second portion.

In any of the aspects above, in addition to the signalling apparatus, the first portion may comprise the timer. The label may further comprise a power source such as a battery to power the timer and the signalling apparatus. The first portion may also comprise the power source. In some embodiments, all electronic elements of the label may be comprised in the first portion.

The first portion may be located towards a first end of the label and the second portion may be located towards a second end of the label, opposite from the first end, along a longitudinal axis of the label. By providing a first portion that comprises the electronic elements and a second portion that comprises the fixing portion, these two key portions of the label may take substantially different forms. For example, the second portion may be maintained as a relatively flexible, flat and/or discreet portion of the label that can be fixed to a number of different support surfaces, including contoured surfaces, while the first portion may be maintained as a relatively inflexible and/or bulky portion suitable for housing the electronics.

As indicated, in some embodiments, the first portion may be separable from the second portion. Provision of first and second portions that are separable can allow the first portion to be removed or disconnected from the support surface (e.g. a surface of medical records, a surface of a container or otherwise) while the second portion remains fixed to the support surface. Various components of the label such as the signalling apparatus may be relatively bulky. Accordingly, by locating components in the first portion and permitting removal of the first portion from the second portion, e.g., after the predetermined time period has expired and the alert signal has been made, the second portion only may remain permanently attached to the support surface. The second portion may be relatively small and/or streamline in comparison to the first portion. In addition to providing for a reduction in size of the label, removal of the first portion may provide a visual indication that the monitoring of the predetermined time period has expired and any necessary action has been taken as a result of its expiry. Moreover, when the signalling apparatus or other electronic elements are located in the first portion, providing the option of removing the first portion from the second portion fixed to a support surface can assist with waste disposal or recycling practices. For example, it may allow the medical records, the container or any other item comprising the support surface to which the second portion of the label is fixed to be disposed of in a first manner that is different from a second manner in which the first portion is disposed of. For example, the first manner of disposal may employ general recycling, standard waste bins, paper shredders or otherwise, whereas the second manner of disposal may employ e-waste recycling, etc.

By maintaining fixation of the second portion to the support surface, the second portion may provide a record in relation to the monitoring of the predetermined time period that remains part of the support surface, e.g. part of the medical records, the surface of a container or otherwise. For example, the second portion may comprise a display portion to provide information relating to the medical device or other product and/or information relating to the monitored predetermined time period. The display portion may comprise a surface on which a user can write information and/or a surface on which information is pre-printed.

The first portion may be manually separated from the second portion. The label may comprise a frangible element, tear line, tear notch, perforations and/or other region of weakness that enables manual separation of the first and second portions. Thus, the first portion may be torn from the second portion, for example. In addition to or as an alternative to tearing, the first and second potions may be snapped apart, cut apart or otherwise. Cutting may involve use of scissors or other types of cutting elements.

By providing the fixing portion in the second portion, and by providing the signalling apparatus in the first portion, the signalling apparatus may be arranged to overhang an edge of the support surface while the second portion is fixed to the support surface, enabling easier observation of the signalling apparatus, or at least an element thereof.

When the label is used with medical records, and the medical records comprise one or more sheets of paper, the second portion may be affixed to and locate directly over a first piece of paper while at least part of the first portion projects beyond an edge of the first piece of paper. If a second piece of paper were placed on top of the first piece of paper, the second portion of the label may be covered by the paper but the first portion of the label may remain visible. In another example, when the medical records comprise a folder or binder, the second portion may be affixed to and locate directly over paper inside, or a wall of, the folder or binder, while at least part of the second portion projects therefrom. Again, the first portion of the label may be covered while the second portion may remain visible. Accordingly, appropriate monitoring of the predetermined time period may continue, even as medical records are modified by a user.

When the label is used with a product located in a container, e.g., a first container, the second portion may be affixed to and locate directly over a support surface of the first container while at least part of the first portion projects beyond the first container. If a second container or other object is placed in close proximity to the first container, the second portion of the label may be covered by that second container or other object but the first portion of the label may remain visible. Accordingly, appropriate monitoring of the predetermined time period may continue.

Following from this, according to one aspect of the present disclosure, there is provided a label comprising:

a timer to monitor a predetermined time period relating to a product;

a signalling apparatus that provides an alert signal on expiry of the predetermined time period; and a fixing portion to fix the label to a support surface, wherein the label comprises a first portion and a second portion, and wherein the signalling apparatus is comprised in the first portion and the fixing portion is comprised in the second portion, and wherein the first portion is configured to overhang the support surface when the fixing portion fixes the label to the support surface.

In any of the preceding aspects, the signalling apparatus may comprise one or more signalling elements that produce the alert signal. Signalling elements may comprise any one or more of a display, a loudspeaker, a vibration means, and a light, for example. The alert signal may comprise any one or more of an audible signal, a visual signal and a tactile signal, for example. The display may comprise any one or more of an LCD display, LED display, plasma display and E-ink display, for example. The light may comprise an LED or light bulb, for example.

When a display is provided, the display may provide an indication of the degree to which the predetermined time period has elapsed following commencement of monitoring of the predetermined time period (e.g., a countdown of time, a count up of time or other visual indicator). Where the display is used to provide an alert signal upon expiry of the predetermined time period, the display may flash or provide some other readily identifiable warning signal.

When a loudspeaker is provided, the loudspeaker may issue an alert signal by sounding, e.g., by beeping loudly.

When a light is provided, the light may issue an alert signal by turning on, turning off or flashing on and off.

A first type of alert signal may be issued prior to expiry of the predetermined time period and a second type of alert signal may be issued upon expiry of the predetermined time period. The first type of alert signal may indicate that the predetermined time period is being monitored prior to expiry, whereas the second type of alert signal may indicate that the predetermined time period has expired. The first type of alert signal may therefore be different from the second type of alert signal.

The first type of alert signal may be continually emitted prior to expiry of the predetermined time period, periodically emitted prior to expiry, or emitted only upon an actuation step being carried out by the user. The second type of alert signal may be continually emitted upon expiry of the predetermined time period, periodically emitted upon expiry of the predetermined time period, or emitted only upon an actuation step being carried out by the user. The actuation step in relation to the first and/or second alert signal may comprise pressing of a button comprised in the label, for example. The actuation step may therefore enable a user to interrogate the status of the label, e.g., to check if the label is still monitoring the time period and/or to check if the predetermined time period has expired. The use of the actuation step may provide an energy saving measure.

In one embodiment, the signalling apparatus comprises one or more lights that emit light of a first colour as the first type of alert signal, e.g., green light, and which emit light of a second colour, e.g., red light, as the second type of alert signal. The first colour light may be emitted automatically upon initiation of the monitoring of the predetermined time period but may remain off for a majority of the predetermined time period thereafter, except when a user carries out the actuation step to interrogate the status of the label. On the other hand, upon expiry of the predetermined period, the second colour light may be emitted continually or periodically over an extended period of time (e.g., until the power source comprised in the label fully discharges), so that a user is readily made aware that the predetermined time period has expired and action in relation to an associated medical device or other product may need to be taken.

In any of the preceding aspects, the fixing portion may comprise adhesive, e.g., an adhesive layer, to fix the label to the support surface. The fixing portion may comprise a backing layer that is removable to expose the adhesive and place the label in a state for fixing to the support surface. Alternative fixing portions may be provided, however, e.g., depending on the nature of the support surface to which the label is to be fixed. For example, the fixing portions may comprise a hook/loop fastener, a magnet, a clip or otherwise. Where first and second portions are provided, in some embodiments the fixing portion may extend on a rear surface of the second portion, but not a rear surface of the first portion.

In embodiments of the present disclosure, a variety of approaches may be taken to cause initiation of monitoring of the predetermined time period by the timer. For example, the label may comprise an actuator such as a button or a slider that is pressed by a user to start the monitoring, or comprise a tab that is removed to start the monitoring. In some embodiments, the fixing portion may be moveable between a first state and a second state. Moving of the fixing portion from the first state to the second state may place the fixing portion in a condition for fixing the label to the support surface and initiate monitoring of the time period by the timer.

Following from this, according to another aspect of the present disclosure, there is provided a label comprising:

a timer to monitor a predetermined time period relating to a product;

a signalling apparatus that provides an alert signal on expiry of the predetermined time period; and a fixing portion to fix the label to a support surface, wherein the fixing portion is moveable between a first state and a second state, wherein moving the fixing portion from the first state to the second state places the fixing portion in a condition for fixing the label to the support surface and initiates monitoring of the predetermined time period by the timer.

As indicated above, the fixing portion may comprise adhesive and a backing layer that is removable to expose the adhesive and place the label in a state for fixing to the support surface. Thus, in some embodiments, the fixing portion may be moved from the first state to the second state by removal of the backing layer from the adhesive and removal of the backing layer may cause initiation of the monitoring of the predetermined time period. The backing layer may be connected to a switch that turns the timer on upon removal of the backing layer. As an alternative, the backing layer or a tab connected to the backing layer, may be interposed between an electrical contact and a terminal of a power source e.g., a battery that powers at least the timer. While it is interposed between the contact and terminal, it may prevent electricity from being supplied to the timer. Upon removal of the backing layer and optional tab, electricity may begin to flow to the timer, causing monitoring of the predetermined time period to start.

A similar approach may be taken where the fixing portion is not involved in initiation of monitoring of the predetermined time period by the timer. For example, a tab may be interposed between a contact and a terminal of the power source, but the tab may accessible to the user such that the user can remove the tab, e.g., by pulling the tab.

In one aspect, the present disclosure provides medical records comprising the label.

The medical records may comprise one or more sheet elements of paper, plastic or card, wherein the label is fixed to the one or more sheet elements.

In another aspect, the present disclosure provides a container comprising the label.

The container may comprise a substance or material that has a specific expiry period or recommended usage period such as an ingestible substance, a pharmaceutical, biologically active agent, monoclonal antibody, disinfectant, foodstuff and/or other substance. The container may be a sealed container that, once opened, should be discarded, or at least have its contents discarded, after the specific expiry or usage period has ended. The container may be a bottle, packet, box, can, sachet or carton, for example. The label may be fixed to an outer surface of the container.

In aspects described above, among other things, a medical device label is disclosed that is adapted to be fixed to medical records of a patient. As indicated, the medical records may be a common type of medical records, comprising sheets of paper located in a folder, for example. Nevertheless, in some embodiments, an article may be provided that is pre-configured to receive the medical device label. In some embodiments, the article may be designed to interact electrically with the medical device label. The article may be a base station for receiving the medical device label, for example. In some embodiments, components of the medical device label as described above may be present in the base station.

Following from this, according to an aspect of the present disclosure, there is provided a monitoring system for a medical device, comprising:

a base station; and a medical device label receivable by the base station;

wherein the monitoring system monitors a predetermined time period relating to a medical device based on receipt of the medical device label by the base station.

The base station may perform the monitoring of the predetermined time period, the label may perform the monitoring of the predetermined time period and/or a combination of the base station and the label may perform the monitoring of the predetermined time period.

According to one aspect of the present disclosure, there is provided a base station configured to receive a medical device label and monitor a predetermined time period relating to a medical device based on the receipt of the medical device label.

According to another aspect of the present disclosure, there is provided a medical device label configured to be received by a base station that monitors a predetermined time period relating to a medical device based on the receipt of the medical device label.

The monitoring system, e.g., the base station of the monitoring system, may include a timer or timing module to monitor the predetermined time period. The timer or timing module may monitor for expiry of the predetermined time period by counting up to or counting down from the predetermined time period.

The base station may be usable with a plurality of different medical devices simultaneously and/or sequentially. A plurality of the medical device labels may be provided, wherein each label is associated with a respective one of the plurality of medical devices. Additionally or alternatively, a plurality of the medical device labels may be provided, wherein each label is associated with the same medical device. The base station may be adapted to receive multiple labels simultaneously and/or sequentially and monitor multiple predetermined time periods based on receipt of the plurality of labels by the base station.

The medical device label may comprise a display portion. The display portion may include information about the associated medical device and/or the predetermined time period. Information may be provided on the display portion in a hand-written or printed format. Additionally or alternatively, the display portion may comprise an electronic display, e.g., an LCD or E-ink display, that displays the information.

The label may be designed for disposal after expiry of the predetermined time period. The label may be a single-use label. On the other hand, the base station may be re-used after expiry of the predetermined time period.

The base station may be patient-specific. In this regard, where multiple labels are received by the base station, each label may be associated with a medical device that is used in relation to the same patient. Alternatively, the base station may be usable in relation to multiple patients.

The label and the base station may comprise electrical components. The base station and the label may comprise electric contacts that contact each other and establish electrical communication between the base station and the label when the label is received by the base station. The monitoring system, e.g., the base station of the monitoring system, may monitor the predetermined time period upon establishment of an electrical connection between electrical components of the base station and the label. Monitoring may start automatically on establishment of the electrical connection or following further action by the user, such as the pressing of a button that is optionally included in the base station or label. The base station and the label may comprise electric contacts that contact each other to establish electrical communication between the base station and the label when the label is received by the base station. Alternatively, the base station and the label may comprise induction coils that inductively couple with each other to establish electrical communication between the base station and the label when the label is received by the base station.

Information about the predetermined time period may be comprised in the base station. For example, the base station, e.g. a timer in the base station, may be preconfigured with the predetermined time period. This may be appropriate if the base station is to be used with a medical device or medical devices for which only one predetermined time period is relevant.

Additionally or alternatively, information about the predetermined time period may be comprised in the label. The base station may identify the predetermined time period based on information provided by the label. The base station may identify the predetermined time period at least partially based on receipt of the label. This may be appropriate if the base station is to be used with a medical device or medical devices for which a variety of different predetermined time period are relevant. Information may be provided from the label to the base station via an electrical signal, an optical signal, a wireless signal, and/or by a shape or configuration of the label or otherwise.

To enable information to be provided from the label to the base station by virtue of an electrical signal, an electrical connection between the label and the base station may be established on receipt of the label by the base station. Information about the predetermined time period may be encoded in an electrical signal sent from the label to the base station. A digitally encrypted signal may be provided by the label, e.g., from an electronics chip comprised in the label, to the base station and the base station may decode the digital signal to obtain information about the predetermined time period. Alternatively, the electrical signal may be a measurement signal. The base station may identify the predetermined time period by performing a measurement in relation to the label. For example, one or more electrical components of the base station may measure an electrical property of one or more electrical components of the label and identify the predetermined time period based on the measurement. For example, the label may comprise one or more resistors. An electrical signal may be transmitted across the one or more resistors and the voltage drop across the one or more resistors may be determined by the base station. Depending on the size of the voltage drop, and therefore the size of the resistor, the base station may identify the predetermined time period. Through use of a resistor to provide information about the predetermined time period, rather than e.g., a digitally encrypted signal provided by an electronics chip, the label may be better configured for sterilisation, using processes such as gamma radiation. Subjecting the label to a gamma radiation sterilisation process could corrupt any digital information stored in the label, but would not cause a change in the resistance of the resistor.

To enable information to be provided from the label to the base station by virtue of an optical signal, the base station may comprise a reader that is adapted to read an identifier on the label. The identifier may be a barcode or QR code, for example, and the reader may be configured to scan the identifier. The reader may read the identifier upon receipt of the label by the base station, or prior to or after receipt of the label.

To enable information to be provided from the label to the base station by virtue of a wireless signal, the label may comprise a transmitter and the base station may comprise a receiver. Radio-frequency signals or blue-tooth signals, etc., which contain information about the predetermined time period, may be transmitted from the label to the base station.

To enable information to be provided from the label to the base station by a shape or configuration of the label, the base station may be configured to sense a shape or configuration of the label upon receipt of the label. Different sensed shapes or configurations of the label may be indicative of different predetermined time periods.

One of the base station and the label may comprise a power source, e.g., a battery. The power source may power electrical components of the base station and the label. The power source may be located in the label yet may power electrical components of the base station. In some instances, the base station may not comprise a power source. It can be particularly advantageous to provide the power source in the label to ensure that a power source with a sufficiently high stored energy level is present in the monitoring system at the time that monitoring of the predetermined time period is required. Since a label may be configured for single use only, the energy available from the power source can be expected to be at a relatively high level when the label is used. On the other hand, if the power source is comprised in the base station, to the extent that the base station is usable multiple times with a plurality of different labels, for example, there is a greater possibility that the stored energy would be at a relatively low level. The power source may therefore have insufficient energy to power electrical components for the duration of the predetermined time period. While the power source may be replaceable or rechargeable, or the base station may be connected to a mains supply, convenience to the user may be increased through provision of the power source within the label.

The monitoring system may have a substantially planar shape. The base station and/or the label may have a substantially planar shape. By having a substantially planar shape, storage of the monitoring system and/or components thereof may be straightforward. The monitoring system may be locatable in a holder, e.g., a document holder such as a medical records holder, which may be located at the end of a patient's bed or otherwise. The records holder may be a folder such as a ring binder. In one embodiment, the base station is a ring binder insert. The base station may include a plurality of holes for engaging rings of the ring binder. The monitoring system may be locatable in other types of holders, however, such as a wall-mounted holder or a desk-mounted holder. In some healthcare environments, it is known to write patient records or general patient data on a whiteboard. The monitoring system may be locatable in a holder that is mounted on or adjacent to a whiteboard.

By configuring the monitoring system for location within a holder, such as a medical records holder, the monitoring system may be readily accessible by the user (e.g., a nurse, doctor or clinician, etc.), and held in a secure location at least during the duration of monitoring of the predetermined time period. In accordance with discussions above, the monitoring system may comprise signalling apparatus that provides an alert signal on expiry of the predetermined time period. Additionally, an alert signal may be provided by the signalling apparatus at one or more scheduled times in the lead-up to expiry of the predetermined time period or subsequent to expiry of the predetermined time period.

The base station may comprise the signalling apparatus or the label may comprise the signalling apparatus, or the signalling apparatus may be shared by the base station and the label. Additionally or alternatively, the signalling apparatus may be partially or entirely comprised in an external device that is separate from the base station and the label, such as a computer device. The monitoring system may communicate with the external device via a communications network, e.g., via the internet, Wi-Fi, Bluetooth, or otherwise. The computer device may form part of a computer system of a hospital or clinic, etc., where the monitoring system is used.

The signalling apparatus may comprise one or more signalling elements that produce the alert signal. Signalling elements may comprise any one or more of a display, a loudspeaker, a vibration means, and a light, for example. The alert signal may comprise any one or more of an audible signal, a visual signal and a tactile signal, for example. The display may comprise any one or more of an LCD display, LED display, plasma display and E-ink display, for example. The light may comprise an LED or light bulb, for example.

When a display is provided, the display may provide an indication of the degree to which the predetermined time period has elapsed following commencement of monitoring of the predetermined time period (e.g., a countdown of time, a count up of time or other visual indicator). Where the display is used to provide an alert signal upon expiry of the predetermined time period, the display may flash or provide some other readily identifiable warning signal.

When a loudspeaker is provided, the loudspeaker may issue an alert signal by sounding, e.g., by beeping loudly.

When a light is provided, the light may issue an alert signal by turning on, turning off or flashing on and off.

In one embodiment, the signalling apparatus comprises the display and the light, which are each configured to provide an alert signal simultaneously upon expiry of the predetermined time period.

As indicated, the base station may be adapted to receive a plurality of the labels at the same time. In this instance, the signalling apparatus may comprise multiple signalling elements, a different one of the signalling elements being used in relation to each one of the labels. By taking this approach, a user may be able to identify which of a plurality of different time periods being monitored simultaneously has or have expired, and/or the degree to which those predetermined time periods have elapsed. In one embodiment, the signalling apparatus comprises multiple displays, each display being for use with a respective one of the labels.

The base station may comprise a receiving portion and the label may comprise an engagement portion. The base station may receive the label by virtue of engagement, e.g., releasable engagement, between the receiving portion and the engagement portion. One of the receiving portion and the engagement portion may comprise a recess and the other of the receiving portion and the engagement portion may comprise a protrusion that is adapted to be received in the recess to achieve the engagement. For example, the receiving portion may comprise the recess and the engagement portion may comprise the protrusion. The receiving portion may be held in engagement with the engagement portion by virtue of a friction fit. Additionally or alternatively, the receiving portion may be held in engagement with the receiving portion by adhesion, hook-and-loop fastening, magnetism or otherwise.

The receiving portion and the engagement portion may each comprise electrical contacts that form an electrical connection between the base station and the label upon engagement between the receiving portion and the engagement portion. Transfer of power and/or information between the base station and the label may be via the electrical connection.

When the base station is configured for use with multiple labels, the base station may comprise a plurality of the receiving portions, each adapted to engage with an engagement portion of a respective one of the labels.

The label may comprise a housing and an electronics unit located in the housing. The housing may define the engagement portion of the label. The label may comprise the display portion adapted to display information about the medical device and/or predetermined time period. The housing may protrude relative to the display portion. The display portion may be removable from a portion of the label that comprises the housing. The label may comprise a tear line to enable the removal of the display portion. The display portion may comprise an adhesive, e.g., on an outer surface thereof. Removal or separation of the display portion can allow the display portion to be placed in medical records of a patient, or placed in a different part of medical records of a patient, after use of the label. The adhesive may enable attachment of the display portion to medical records.

According to one aspect of the present disclosure, there is provided a medical device label comprising a power source and an engagement portion, the engagement portion being adapted to engage a receiving portion of a base station to establish an electrical connection between the power source and the base station.

The label of this aspect may comprise any one or more features of the label described above with respect to preceding aspects.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

By way of example only, embodiments are now described with reference to the accompanying drawings, in which:

FIG. 5 shows a front oblique view of the label with the backing layer completely peeled off but with the backing layer connected to the remainder of the label by a tab;

FIG. 6 shows a front oblique view of the label with the backing layer completely peeled off and the tab removed from the remainder of the label;

FIG. 10c shows a rear oblique view of an electronics unit of the label of FIG. 10a;

FIG. 11a shows an oblique view of a medical device monitoring system, including a base station and a label, according to an embodiment of the present disclosure, the monitoring system being located in a patient records holder; and FIG. 11b shows a cross-sectional view of the monitoring system along line A-A in FIG. 11a;

FIG. 12 shows an oblique exploded view of the monitoring system of FIG. 11a;

FIGS. 13a, 13c and 13d show front, side and rear views, respectively, of the label of FIG. 10a; and FIG. 13b shows a cross-sectional view of the label along line A-A in FIG. 13a;

FIG. 14 shows an oblique exploded view of the label of FIG. 11a;

FIGS. 15a and 15b show front and rear views, respectively, of an electronics unit of the label of FIG. 11a;

FIG. 16 shows a schematic illustration of various electrical components of the monitoring system of FIG. 11a;

DESCRIPTION OF EMBODIMENTS

Figure 1A:
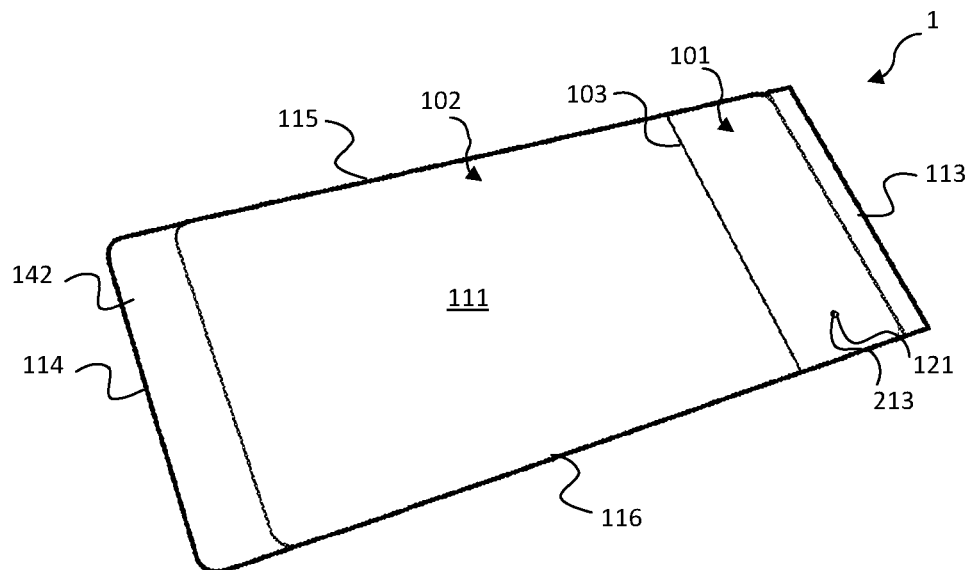
FIGS. 1a and 1b shows front and rear oblique views of a label according to an embodiment of the present disclosure.
Figure 1B:
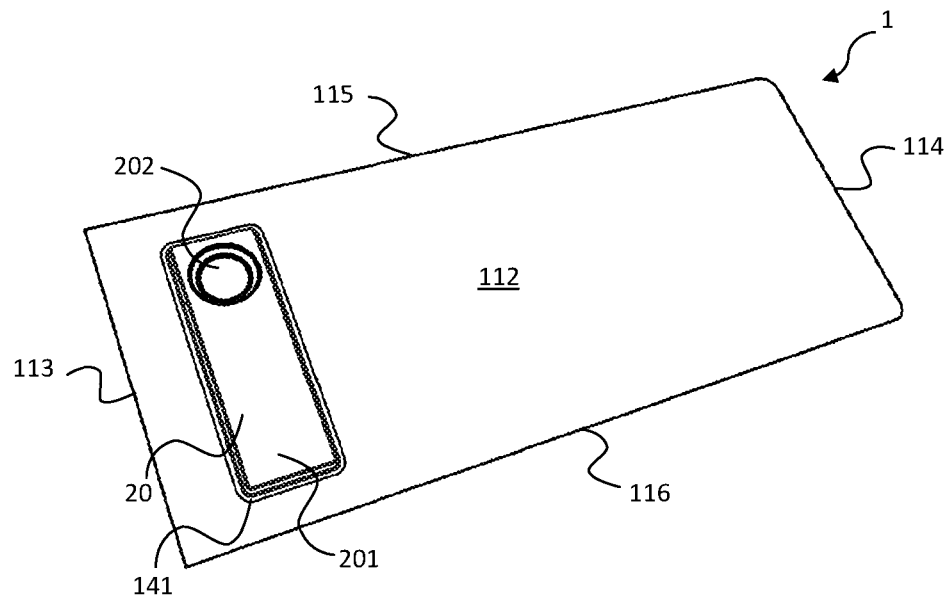

Oblique front and rear views of a label 1 according to an embodiment of the present disclosure are shown in FIGS. 1a and 1b. The label 1 includes a timer to monitor a predetermined time period relating to a product and specifically, in the present embodiment, a medical device. The label may therefore be considered a medical device label 1. The label 1 includes a signalling apparatus that provides an alert signal on expiry of the predetermined time period, and a fixing portion to fix the label to medical records of a patient.

The medical device label 1 in this embodiment is associated with a medical device such as an intravascular cannula that is to be inserted in a patient for a period of time, e.g., in a hospital environment. The label can be packaged with the medical device prior to use of the label and medical device. A cannula is an example of an invasive medical device that should be located in a patient for no longer than a maximum safe period (e.g., 24 hours, 72 hours, 7 days or otherwise), as governed by medical standards, protocols or regulations applicable to the environment where it is used (e.g., hospital, ambulance or clinic, etc.), or manufacturer's guidelines for the medical device. By limiting indwelling of a medical device such as a cannula to a maximum safe period or less, the risk of the patient contracting a HAI can be significantly reduced.

Following from this, in the present embodiment, the timer is adapted to monitor a predetermined time period (e.g., 24 hours) that corresponds to the maximum safe period for indwelling of an associated medical device. The monitoring of the predetermined time period is triggered by a user action in relation to the label as discussed further below. Monitoring of the predetermined time period may comprise counting up or counting down the predetermined time period using the timer.

The medical device is not necessarily an invasive, indwelling device or a device prone to causing infection, however. In alternative embodiments, the medical device label may be associated with any medical device for which monitoring of a predetermined time period is desirable. For example, the medical device may be a compression bandage or a drug delivery patch that should be removed within a specific period of time. As another example, the medical device may be a hospital bed, wherein a patient lying on the bed should be encouraged to move periodically to avoid pressure sores. Moreover, in alternative embodiments, the label 1 may be used to monitor other products such as a substance or material that has a specific expiry period or recommended usage period. For example, the product may be an ingestible substance, a pharmaceutical, a biologically active agent, a monoclonal antibody, a disinfectant, a foodstuff and/or any other substance or material that has a specific expiry or usage period. Further discussion of such use of the label is provided further below with reference to FIG. 18.

Referring to FIGS. 1a and 1b, the label 1 has a substantially planar configuration, with substantially rectangular front and rear surfaces 111, 112, a first end 113, a second end 114, a first side 115 and a second side 116. The length direction of the label 1 extends between the first and second ends 113, 114 and the width direction of the label extends between the first and second sides 115, 116.

Figure 2:
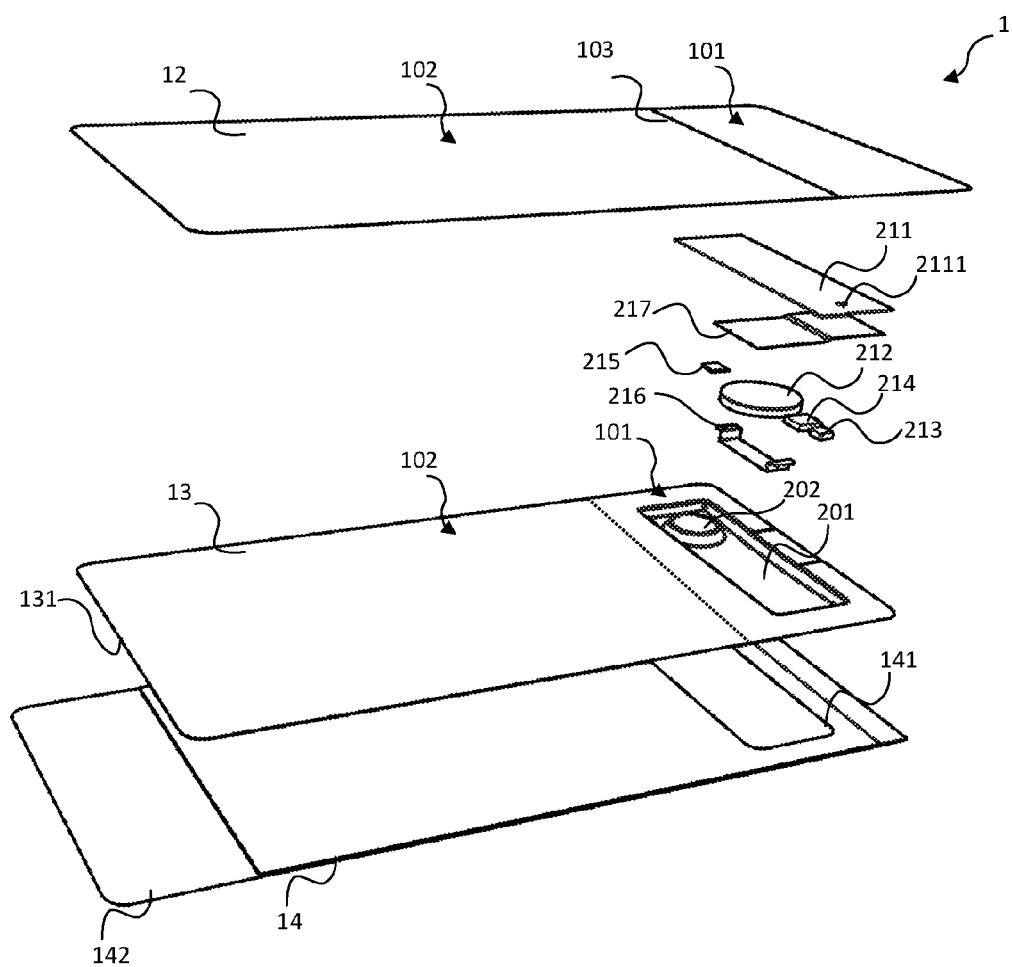
FIG. 2 shows an exploded view of the label.

As can be seen from the exploded view of FIG. 2, the label 1 generally has a three-layer construction, including a front panel 12, a rear panel 13 and a releasable backing layer 14. The rear panel 13 includes adhesive on a rear surface 131 thereof, which is covered prior to use by the releasable backing layer 14. Release of the backing layer 14 exposes the adhesive, enabling the rear surface 131 to be fixed to medical records or another support surface. In this regard, the adhesive provides part of a fixing portion of the label.

In the length direction of the label, the front and rear panels 12, 13 are each divided into a first portion 101 and a second portion 102, the first and second portions 101, 102 being located at opposite sides of a tear line 103. The first portion 101 is located toward the first end 113 of the label and the second portion 102 is located towards the second end of the label 114. The tear line extends between the first and second sides 115, 116 of the label 1 in the width direction of the label 1. The first portion 101 is smaller than the second portion 102. Both the first portion 101 and the second portion 102 extend across the full width of the label 1. The second portion 102 extends across a greater portion of the label 1 in the length direction of the label 1 than the first portion 101. The first portion 101 is separable from the second portion 102 by virtue of a user tearing along the tear line 103.

The label 10 is substantially flat, except at a region of the second portion 102 of the label 1 where the label 1 includes a housing 20 for an electronics unit 21. The housing 20 is formed by a section of the front panel 12 and an opposing relief 201 formed in the rear panel 13, the relief 201 projecting rearward relative to the remainder of the rear panel 13. The backing layer 14 includes an opening 141 through which the housing 20 projects. The relief 201 is shaped to both enclose the electronics unit 20 and form a button 202 that is accessible by a user.

Figure 3:
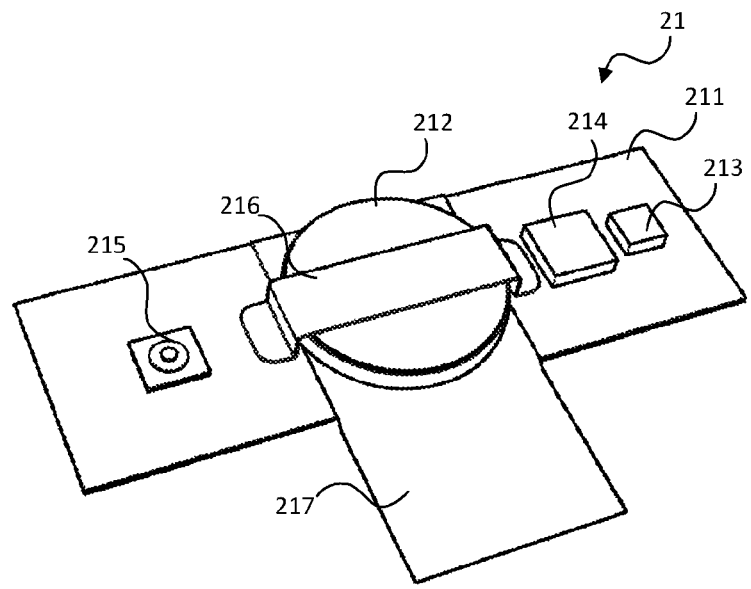
FIG. 3 shows a rear oblique view of an electronics unit of the label.

With reference to FIGS. 2 and 3, the electronics unit 21 located in the housing 20 comprises a printed circuit board (PCB) 211 on which a battery 212 is mounted along with an LED 213, a processor (microchip) 214 and a test switch 215, the test switch 215 being positioned underneath the button 202 in the relief 201. The battery 212 provides a source of power for the LED 213 and processor 214. Electricity is transferred to the LED 213 and processor 214 via an electrical circuit including the PCB 211. The electrical circuit is connected to the battery 212 by a first electrical contact (not visible) and a second electrical contact 216. The first electrical contact is positioned on the PCB 211, underneath the battery 212, to electrically contact a first terminal of the battery 212. The second electrical contact 216 is in the form of a flexible conductive arm and forms a bridge from the PCB 211 over the battery 212 to electrically contact a second terminal of the battery 212. The second electrical contact 216 also clips the battery 212 in place, holding it firmly in position against the PCB 211.

As can be seen most easily in FIG. 3, a removable, non-conductive tab 217 is positioned under the battery between the first terminal of the battery 212 and the first electrical contact of the PCB 211. While the tab 217 remains in this position, the first electrical contact is insulated from the first terminal of the battery 212 by the tab 217 and the electrical circuit is therefore incomplete (open). In this state, electricity cannot flow from the battery 212 to the processor 214 and LED 213. However, when the tab 217 is removed, the first terminal of the battery 212 and the first electrical contact are configured to touch so as to complete (close) the electrical circuit. When complete, electricity can flow from the battery 212 to the processor 214 and LED 213. The LED 213 is visible at the front surface 111 of the label 1 through a small window 121 in the front panel 12 that aligns with a small window 2111 in the PCB 211, adjacent the mounting position of the LED 213 on the PCB 211. The LED 213 forms part of signalling apparatus that provides an alert signal on expiry of the predetermined time period, as discussed further below.

Figure 9:
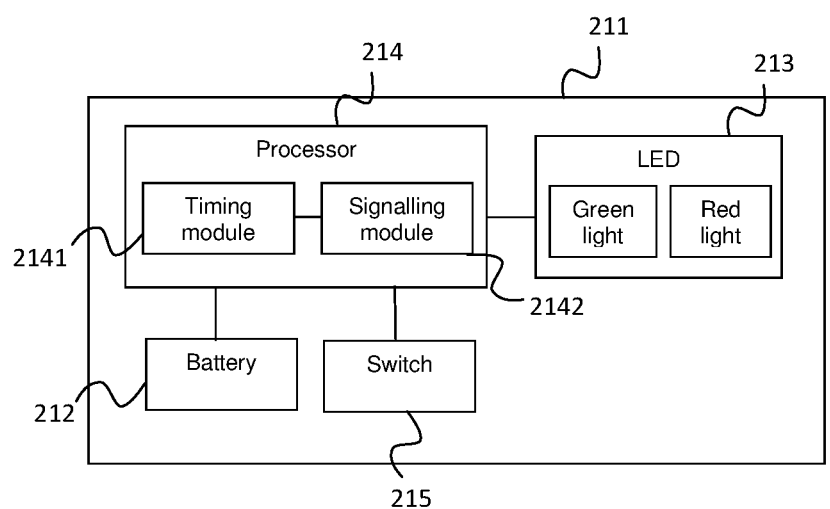
FIG. 9 shows a schematic illustration of components of the electronics unit of the label.

In this embodiment, removal of the tab 217 provides a trigger for the timer to start monitoring the predetermined time period. The timer is provided by a timing module 2141 within the processor 214, and is configured to start timing when electricity is supplied to the processor 214 from the battery 212. The timing module 2141 is represented in FIG. 9, which provides a schematic illustration of electrical components of the label 1.

Figure 4:
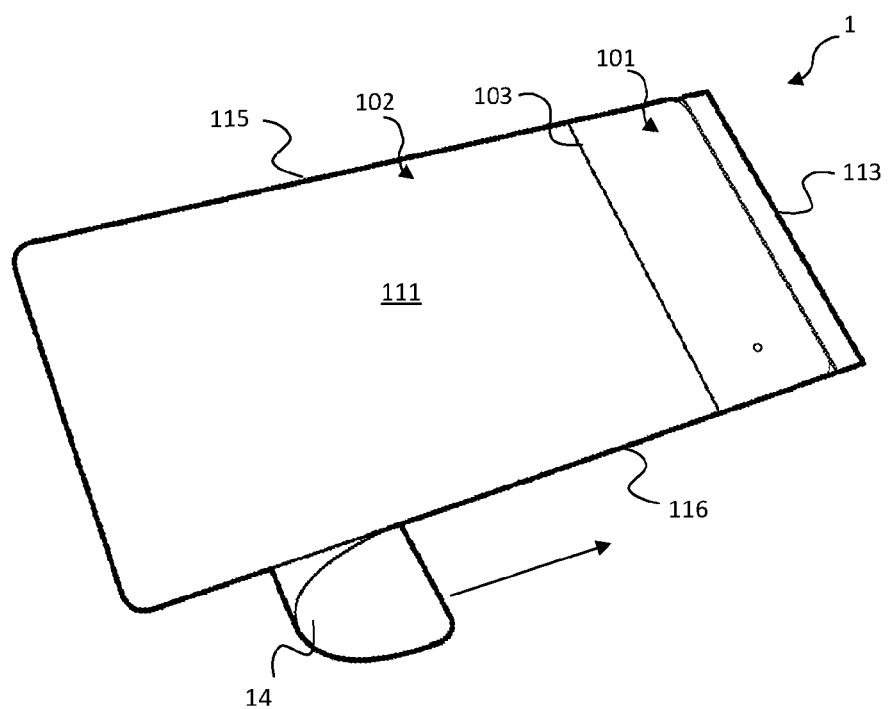
FIG. 4 shows a rear oblique view of the label with a backing layer partially peeled off.

The label 1 is configured so that removal of the backing layer 14 from the label 1 causes the removal of the tab 217 from its position underneath the battery 212. The tab 217 is connected to the backing layer adjacent the first end 113 of the label 1. At the opposite end 114 of the label 1, the backing layer 14 includes a grip portion 142 that projects beyond the first and second panels 12, 13 of the label. The grip portion 142 is easily accessible and engageable by the user. To start using the medical device label, a user can take hold of the grip portion 142 to peel the backing layer 14 from the rear panel 14 of the label, in a direction towards the first end 113 of the label 1 as represented in FIG. 4. When the backing layer 14 is initially peeled off the rear panel 13, it remains connected to the front and rear panels 12, 13 of the label via the tab 217 as shown in FIG. 5. However, further pulling of the backing layer 14 pulls the tab 217 from its position underneath the battery 212. This separates the backing layer 14 from the front and rear panels 12, 13 and triggers the monitoring of the predetermined time period as discussed above.

When the backing layer 14 is peeled off it exposes the adhesive on the rear surface 131 of the rear panel 13. The adhesive is positioned only on the rear surface 131 of the second portion 102 of the label 1 and not the first portion 101 of the label 1. The adhesive provides part of a fixing portion to fix the second portion 102 of the label 1 to medical records or other support surface. Removal of the backing layer 14 to expose the adhesive essentially causes the fixing portion to move from a first state to a second state. Only in the second state is the fixing portion made ready to fix the label 1 to medical records or other support surface. Moving of the fixing portion from the first state to the second state, by virtue of removal of the backing layer 14, causes initiation of the monitoring of the predetermined time period as discussed above.

By fixing the label 1 to medical records, for example, the label 1 can be readily accessible by a user and held in a secure location at least during the duration of monitoring of the predetermined time period. In general, a patient's medical records can remain in close proximity to the patient at all times, e.g., through location in a records holder (usually at the end of the patient's bed), and it is therefore readily and regularly accessible by medical staff. A patient's medical records are a source of status information relating to the patient, and therefore an ideal location for the medical device label 1. This contrasts, for example, with placement of a monitoring system such as a timer on medical device(s) attached to the patient, or placement directly on the patient. In these circumstances, the monitoring system may be more prone to damage or interference, or may be more likely to cause damage or interference to other equipment. For example, should the patient need to undergo a MRI scan, it may be necessary to remove any monitoring system placed on the patient, or on medical devices attached to the patient, to avoid interference with MRI apparatus. Further, when the monitoring system is placed on another medical device (e.g., an adhesive dressing or cannula line, etc.) that medical device may need to be replaced before the predetermined time period being monitored has ended, and before it is desirable to end monitoring of the predetermined time period.

Figure 7:
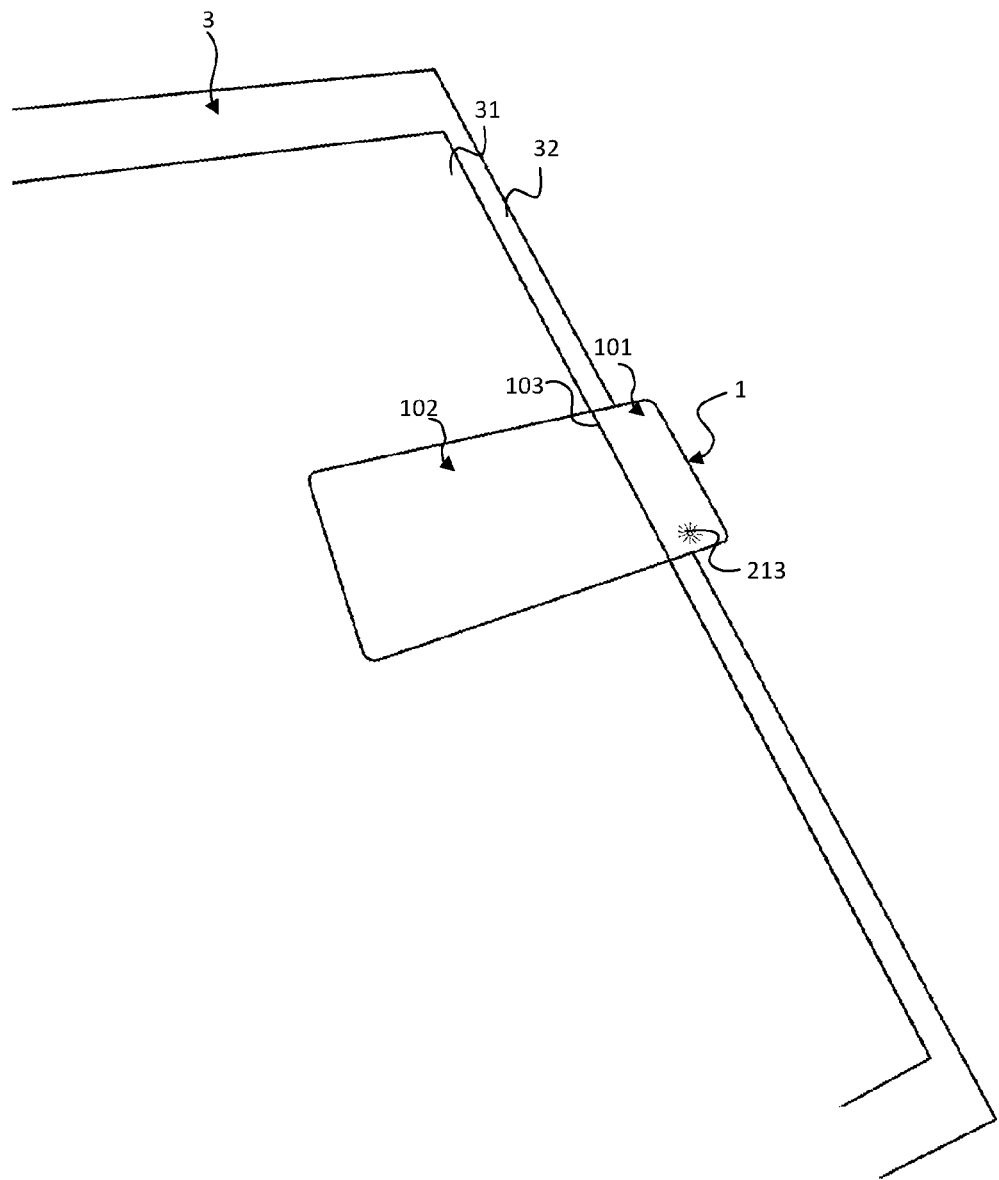
FIG. 7 shows a front oblique view of the label attached to medical records.

FIG. 7 shows the label 1 fixed to medical records 3 that include a sheet of paper 31 held in a folder 32. The second portion 102 of the label 1 is fixed to the sheet of paper 31 while the first portion 101 projects beyond (overhangs) the edge of the paper 31. In this embodiment, the first portion 101 also projects beyond the edge of the folder 32. If another piece of paper were placed on top of the paper 31, the second portion 102 of the label 1 may be covered by the paper but the first portion 101 of the label can remain visible. Accordingly, appropriate monitoring of the predetermined time period may continue, even as medical records are modified by a user.

As indicated, the signalling apparatus that provides an alert signal on expiry of the predetermined time period comprises the LED 213. Referring to FIG. 9, further componentry of the signalling apparatus is provided by a signalling module 2142 in the processor 214. In this embodiment, the LED 213 is a bi-colour LED that is operable to selectively emit red and green light. The red light provides a first type of alert signal and the green light provides a second type of alert signal. After expiry of the predetermined time period as monitored by the timer, the signalling module 2142 causes the LED 213 to emit red light, providing an alert to the user that the predetermined time period has ended and that appropriate action needs to be taken.

After initiation of monitoring of the predetermined time period, and prior to expiry of the predetermined time period, the signalling module 2142 is adapted to cause the LED 213 to emit green light. Green light is emitted by the LED 213 for a brief period at the start of monitoring of the predetermined time period (i.e. upon removal of the non-conductive tab 217), but the LED 213 remains off thereafter until an optional actuation step is carried out by the user or until the predetermined time period expires. The actuation step comprises a user pressing the button 202 such as to depress the switch 215 of the electronics unit 21. Pressing of the button 202 enables a user to interrogate the status of the label, e.g., to check if the label is still monitoring the predetermined time period. If the button 202 is pressed while the predetermined time period is being monitored, prior to expiry of the predetermined time period, the LED 213 will emit green light. By emitting green following user interrogation, rather than continuously up to expiry of the predetermined time period, energy usage from the battery 212 can be reduced. Reducing energy usage reduces the risk that the battery 212 will discharge prior to expiry of the predetermined time period.

Upon expiry of the predetermined period, the red light is emitted from the LED 213 in a flash or continuous mode for an extended period of time (e.g., until the battery 212 fully discharges). This ensures that a user is readily made aware that the predetermined time period has expired and that action in relation to an associated medical device needs to be taken.

In alternative embodiments, e.g., where there is sufficient battery power, the green light may remain on during monitoring of the predetermined time period or may flash intermittently during monitoring of the predetermined time period. The green light may flash every 30 seconds, for example. In accordance with this, in some embodiments the switch and button may be excluded from the label.

Figure 8:
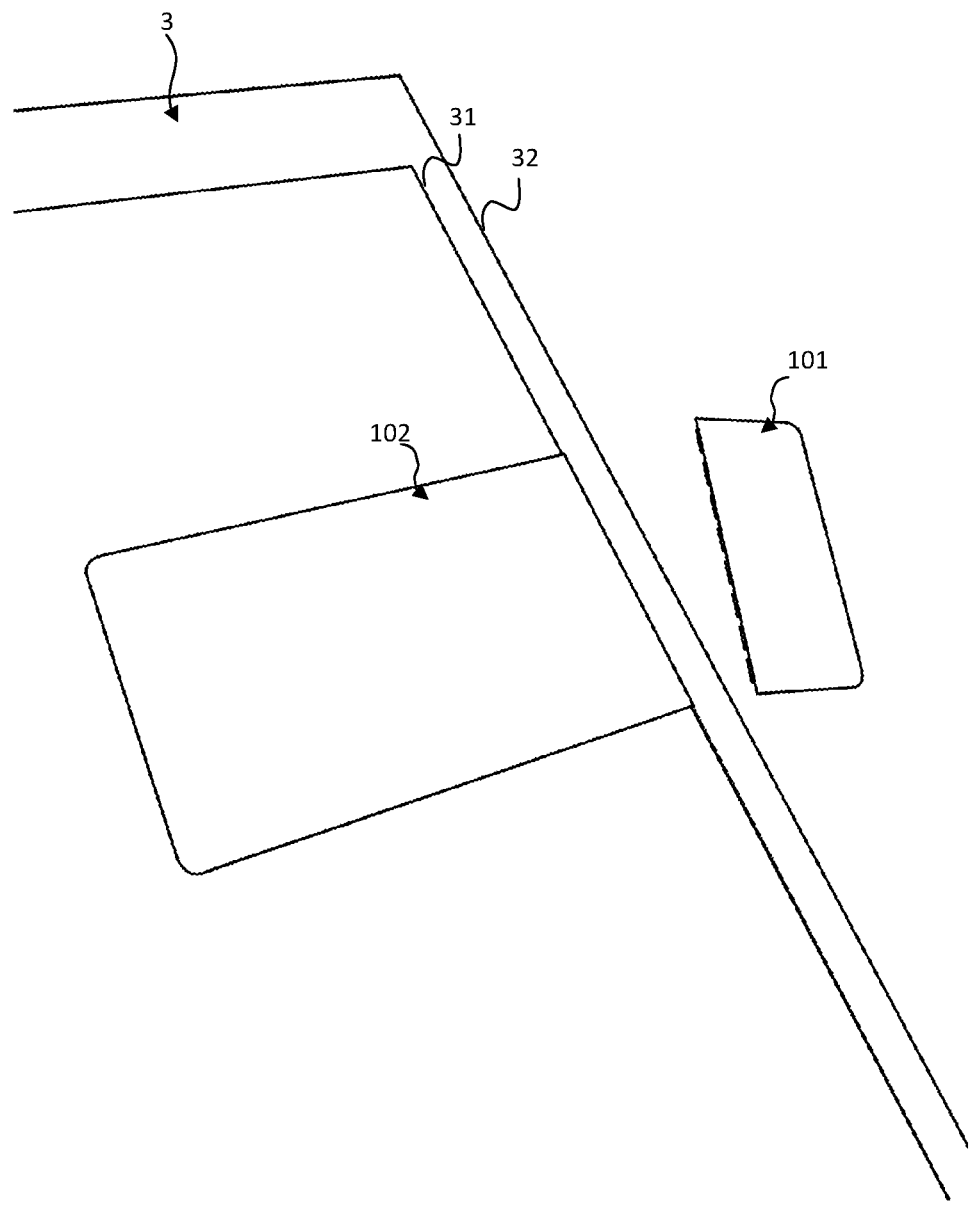
FIG. 8 shows a front oblique view of the label attached to medical records with a first portion of the label removed from a second portion of the label.

As indicated above, through the provision of the tear line 103 between the first and second portions 101, 102 of the label 1, the first and second portions 101, 102 are separable from each other. Separation of the first and second portions 101, 102 is also made possible by the adhesive contact between the label and the medical records 3 occurring at the second portion 102 of the label only. By allowing separation of the first portion 101 from the second portion 102, the first portion 101 can be removed from the medical records 3 after expiry of the predetermined time period and once action in relation to the medical device has been taken. Separation of the first portion 101 from the second portion 102 is represented in FIG. 8. The removed first portion 101 may be discarded. The first portion of the label 101 comprises the relatively bulky housing 20 and electronics unit 21. By removing the first portion 101 including the relatively bulky housing 20 and electronics unit 21, and leaving behind a relatively streamlined second portion 102 of the label 1 only, the medical records 3 may be maintained in a more compact form. Further, removal of the first portion 101 can provide a visual indication to the user that the monitoring of the predetermined time period by the label 1 has expired and any necessary action has been taken as a result of the expiry. Still further, removal of the first portion 101 allows the first portion 101, including the electronics unit 21, to be disposed of in a suitable manner, e.g. using e-waste recycling, while the second portion 102 and the medical records 3 (or any other item to which the label 1 is attached) can be disposed of by other suitable means, e.g. using general recycling, standard waste bins, paper shredders or otherwise.

At the second portion 102 of the label, the front surface 111 of the label provides a surface that includes pre-printed details relating to the medical device associated with the label and the predetermined time period. In an alternative embodiment, all or a part of the front surface of the second portion 102 is left blank, allowing a user to write details thereon. Thus, by maintaining fixation of the second portion 102 to the medical records, the second portion 102 may continue to provide a record relating to the monitoring of the predetermined time period. As an example, when then the medical device is an indwelling device, and the predetermined time period that is monitored by the label 1 corresponds to the maximum period that is considered safe for indwelling of the medical device, the second portion 102 may provide a record of: the time and date of insertion of the medical device into the patient; a name or identifier of the person that inserted the medical device into the patient; the type of the medical device; the positioning of the medical device; and/or the date and time of removal of the medical device.

It will be appreciated by persons skilled in the art that numerous variations and/or modifications may be made to the above-described embodiments, without departing from the broad general scope of the present disclosure.

For example, additional or alternative fixing portions may be provided, e.g., depending on the nature of the medical records or other support surface to which the label is to be fixed. For example, the fixing portions may comprise a hook/loop fastener, a magnet, a clip or otherwise.

As another example, the signalling apparatus may comprise additional or alternative signalling elements that produce the alert signal, such as a display, a loudspeaker and/or vibration means or otherwise. In addition or as an alternative to an audible signal, the alert signal may include a visual signal and/or a tactile signal or otherwise.

As yet another example, alternative approaches may be taken to cause initiation of monitoring of the predetermined time period by the timer. For example, the label may comprise a modified tab, or an actuator such as a button or a slider that is pressed, pulled, or moved by a user to start the monitoring.

Figure 10A:
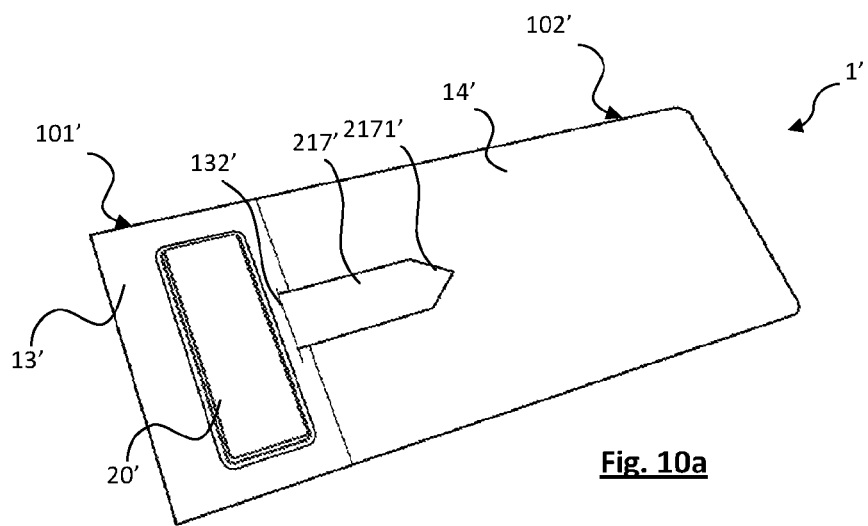
FIG. 10a shows a rear oblique view of a label according to another embodiment of the present disclosure.
Figure 10B:
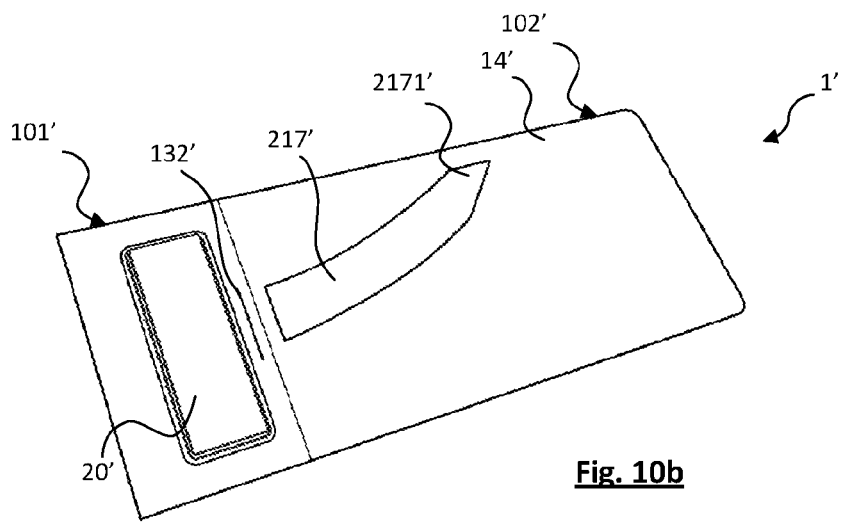
FIG. 10b shows a rear oblique view of the label of FIG. 10a with a tab pulled from the label.
Figure 10C:
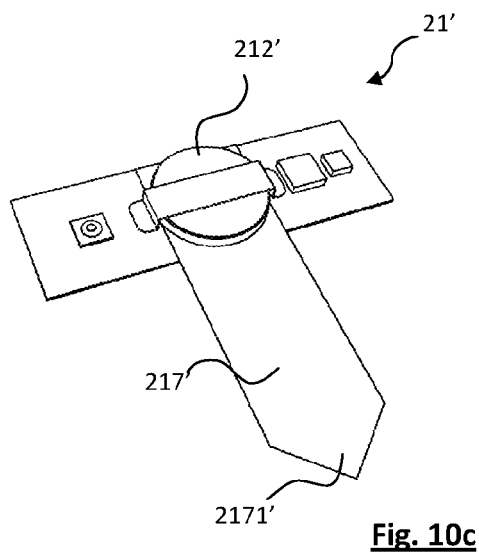

An embodiment of a label 1' according to present disclosure in which the label 1' includes a modified tab 217' is illustrated in FIGS. 10a to 10c. The label 1' is configured in a similar manner to the label 1 of the preceding embodiment as illustrated in FIGS. 1 to 9, with the tab 217' being partially located under a battery 212' to prevent completion of an electrical circuit. The battery 212' forms part of an electronics unit 21' (FIG. 10c), that includes a printed circuit board (PCB) 211' on which the battery 212' is mounted. The electronics unit 21' again locates in a housing 20' of the label 1'. However, in this embodiment, the tab 217' is not connected to a backing layer such that removal of the backing layer causes pulling and therefore removal of the tab. Instead, the tab 217' extends through a slot 132' in a rear panel 13' of the label 1' as illustrated in FIG. 10a, enabling a user to directly engage and pull the tab 217', e.g., with a thumb and forefinger. Pulling the tab 217' from the slot as illustrated in FIG. 10b causes the tab 217' to be released from its location underneath the battery 212' and therefore causes the electrical circuit to be completed. Upon completion of the electrical circuit, the monitoring of the predetermined time period is initiated.

To make it easier for a user to engage the tab 217', the tab 217' is provided with a length greater than the length of the tab 217 shown in FIG. 3, for example. Moreover, to improve usability, an indication of the appropriate direction for pulling of the tab 217' is provided through the forming of pointed end 2171' to the tab 217'. The pointed end 2171' points away from the battery 212'. Additionally or alternatively, indicia may be printed on the tab 217' to assist the user, including words such as "REMOVE TO ACTIVATE" or similar.

In this embodiment, the label 1' again has a first portion 101' and a second portion 102', the first portion 101' being separable from the second portion 102'. Moreover, the label 1' again has primarily a three-layer construction, including a front panel, a rear panel 13' and a releasable backing layer 14' attached to adhesive on the rear panel 13'. However, the adhesive and the backing layer 14' extend over the rear panel 13' at the second portion 102' of the label 1' only, while the tab 217' extends through the slot 132' that is located in the rear panel 13' at the first portion 101' of the label'. Accordingly, the tab 217' and the slot 132' are not obstructed by the adhesive and backing layer 14', ensuring that removal of the tab 217' via the slot 132' is not impeded.

Figure 18:
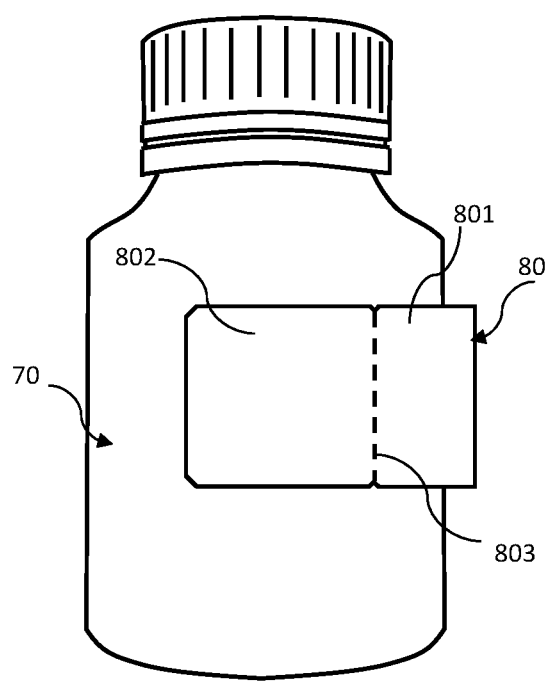
FIG. 18 shows a front view of a container having a label fixed thereto according to another embodiment of the present disclosure.

A front view of a container 70 having a label 80 fixed thereto according to another embodiment of the present disclosure is illustrated in FIG. 18. The label 80 is very similar to the labels 1, 1' described above with reference to FIGS. 1a to 10b. However, so that the label 80 fits more easily on the container 70, the label 80 is provided with a shorter length.

Therefore, like the labels 1, 1' described above, the label 80 includes a first portion 801 and a second portion 802, the first and second portions 801, 802 being located at opposite sides of a tear line 803. The first portion 801 includes some or all of the electronics of the label 80 for monitoring a predetermined time period and issuing an alert signal upon expiry of the time period, and the second portion 802 includes a fixing portion such as an adhesive layer for fixing the label 80 to the container 70. The second portion 802 of the label 80 is fixed to an outer surface of the container 70 that provides a support surface for the label 80. The first portion 801 of the label projects from or overhangs the container 70.

The container 70 houses a product that has a specific expiry or usage period after opening of the container. In particular, in this embodiment, the container 70 is a sealed bottle that contains a liquid pharmaceutical such as an antibiotic that should be discarded, or at least not used, a set number of days after opening of the bottle (e.g., 7 days, 14 days, 28 days after opening or otherwise), preventing use of the pharmaceutical before it becomes overly contaminated, functionally degraded or otherwise inappropriate for consumption. The label 80 is selected to monitor a corresponding time period. Once the time period expires, the label 80 provides the alert signal to a patient, clinician or other user.

Through the provision of the tear line 803 between the first and second portions 801, 802 of the label 80, the first portion 801 can be removed from the container 70, e.g., after expiry of the predetermined time period. The removed first portion 801 may be discarded. Removal of the first portion 801 can provide a visual indication to the user that the monitoring of the predetermined time period by the label 1 has expired and any necessary action has been taken as a result of the expiry and can also assist with waste disposal in accordance with discussions above.

In alternative embodiments of the label 80, however, the first and second portions 801, 802 may not be configured to be separable (they may have no tear line 803, for example). Nevertheless, by providing a first portion 801 that comprises the electronic elements and a second portion that comprises the fixing portion, these two key portions of the label can be maintained in substantially different form. For example, the second portion can be maintained as a relatively flexible, flat and/or discreet portion of the label that is fixable to a relatively contoured support surface of a bottle or otherwise, while the first portion can be maintained as a relatively inflexible and/or bulky portion suitable for housing the electronics.

An oblique view of a medical device monitoring system 4 according to another embodiment of the present disclosure is shown in FIG. 11a. The monitoring system 4 includes a base station 40 and a medical device label 50 that is receivable by the base station 40. In this embodiment, the base station 40 is in the form of a ring binder insert having a substantially planar shape, and includes a plurality of holes for engaging rings 61 of a ring binder 60.

The medical device label 50 is associated with a medical device such as an intravascular cannula that is to be inserted in a patient for a period of time, e.g., in a hospital environment. The label 50 can be packaged with the medical device prior to use of the label and medical device. A cannula is an example of an invasive medical device that should be located in a patient for no longer than a maximum safe period (e.g., 24 hours, 72 hours, 7 days or otherwise), as governed by medical standards, protocols or regulations applicable to the environment where it is used (e.g., hospital, ambulance or clinic, etc.), or manufacturer's guidelines for the medical device. By limiting indwelling of a medical device such as a cannula to a maximum safe period or less, the risk of the patient contracting a HAI can be significantly reduced.

The base station 40 is adapted to monitor a predetermined time period based on receipt of the label 50 by the base station 40. In this embodiment, the predetermined time period that is monitored is the maximum safe period for indwelling of the medical device.

The medical device is not necessarily an invasive, indwelling device or a device prone to causing infection, however. In alternative embodiments, the medical device may be any medical device for which monitoring of a predetermined time period is desirable. For example, the medical device may be a compression bandage or a drug delivery patch that should be removed within a specific period of time. As another example, the medical device may be a hospital bed, wherein a patient lying on the bed should be encouraged to move periodically to avoid pressure sores.

Figure 12:
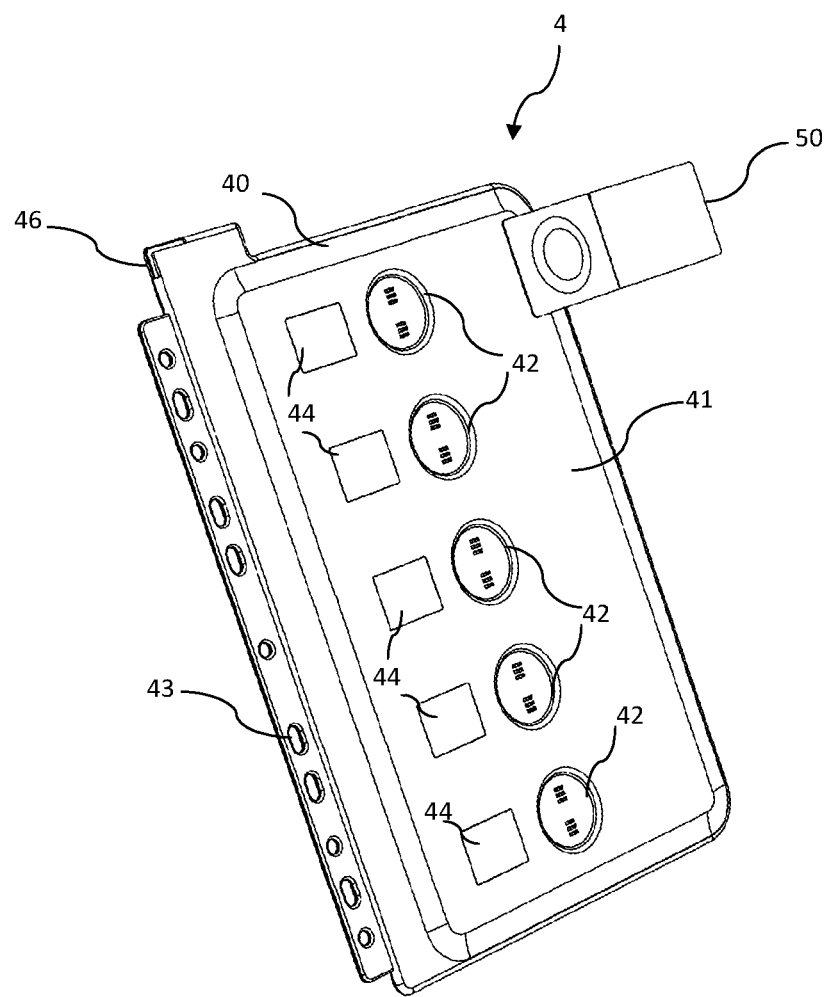

An exploded oblique view of the monitoring system 4 including the base station 40 and label 50 is provided in FIG. 12. FIGS. 13a to 13d provide further views of the label 50. The label 50 has a substantially planar shape with a front surface 511, a rear surface 521, a first end 53 and a second end 54. Each of the front and rear surfaces 511, 521 is substantially flat, except at regions toward the first end 53 of the label 50, where the label includes a housing 55 for an electronics unit 56. The housing 55 is provided in a first portion 581 of the label located towards the first end 53. A second portion 582 of the label 50 is located towards the second end 54 and is separable from the first portion 581 by tearing along a tear line 583. At the second portion 582, the front surface 511 of the label 50 provides a surface that includes pre-printed details relating to the medical device associated with the label and the predetermined time period. In an alternative embodiment, all or a portion of the front surface of the second portion may be left blank, allowing a user to write details thereon. In general, the second portion 582 may be considered a display portion of the label.

Figure 14:
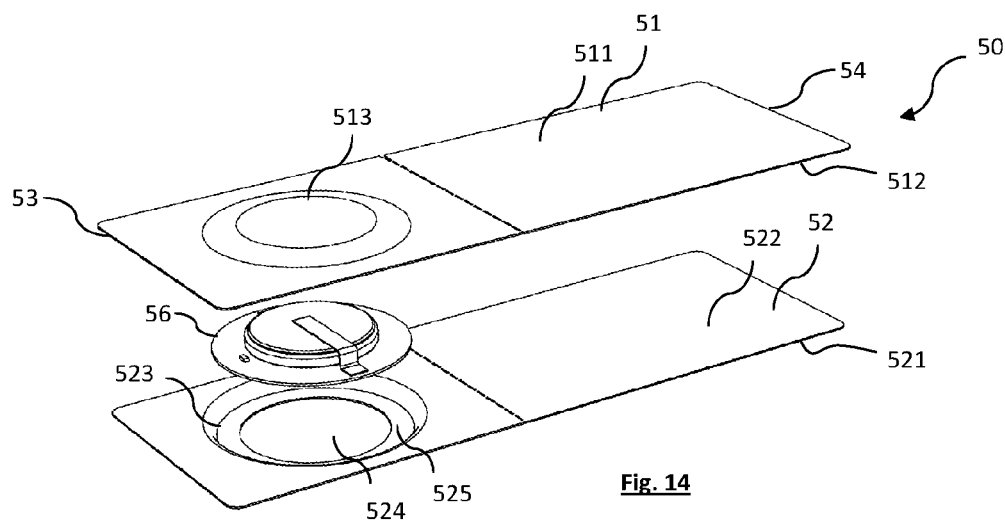

An exploded view of the label 50 is shown in FIG. 14. The label includes a front panel 51 that defines the front surface 511 of the label 50. On an opposite side of the front surface 511, the front panel 51 has an inner surface 512. The label 50 also has a rear panel 52 that defines the rear surface 521 of the label 50. On an opposite side of the rear surface 521, the rear panel 52 has an inner surface 522. The inner surfaces 512, 522 of the front and rear panels 51, 52 are adapted to contact (e.g., adhere to) each other to form the label 50, whereupon the housing 55 is assembled and the electronics unit 56 is securely held within the housing 55.

The housing 55 is defined by a circular relief 513 in the front panel 51 that is raised with respect to the front surface 511 of the front panel 51, and a circular relief 523 in the rear panel 52 that is raised with respect to the rear surface 521 of the rear panel 52. The circular relief 523 in the rear panel 52 has an opening 524, surrounded by a rim 525.

Figure 15A:
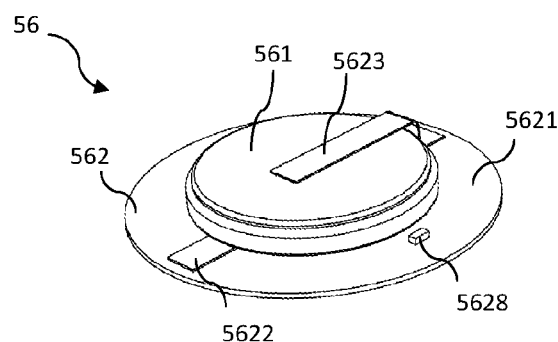
Figure 15B:
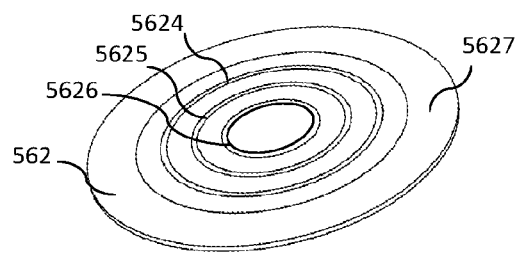

The electronics unit 56 is shown in more detail in FIGS. 15a and 15b and includes a battery 561 and a printed circuit board (PCB) 562, the battery 561 being mounted on an inner surface 5621 of the PCB 562. A first electrical contact 5622 is positioned on the inner surface 5621 of the PCB 562, and locates underneath the battery 561 and electrically contacts a first terminal of the battery 561. A second electrical contact 5623, in the form of a resiliently flexible conductive arm, projects from the inner surface 5621 of the PCB 562, and extends over the battery 561 and electrically contacts a second terminal of the battery 561. The second electrical contact 5623 clips the battery 561 in place, holding it against the inner surface 5621 of the PCB 562. The electronics unit 56 includes first, second and third circular contacts 5624, 5625, 5626 positioned concentrically on the outer surface 5627 of the PCB 562. The first electrical contact 5622 is electrically connected to the first circular contact 5624 and the second electrical contact 5623 is electrically connected to the second circular contact 5625.

An additional electrical component, in particular a resistor 5628, is provided on the PCB 562 to provide information to the base station about the predetermined time period. First and second terminals of the resistor 5628 are electrically connected to the first and third circular contacts 5624, 5626. In this regard, the first circular contact 5624 provides an electrical ground contact for both the battery 562 and the resistor 5628.

Figure 13:
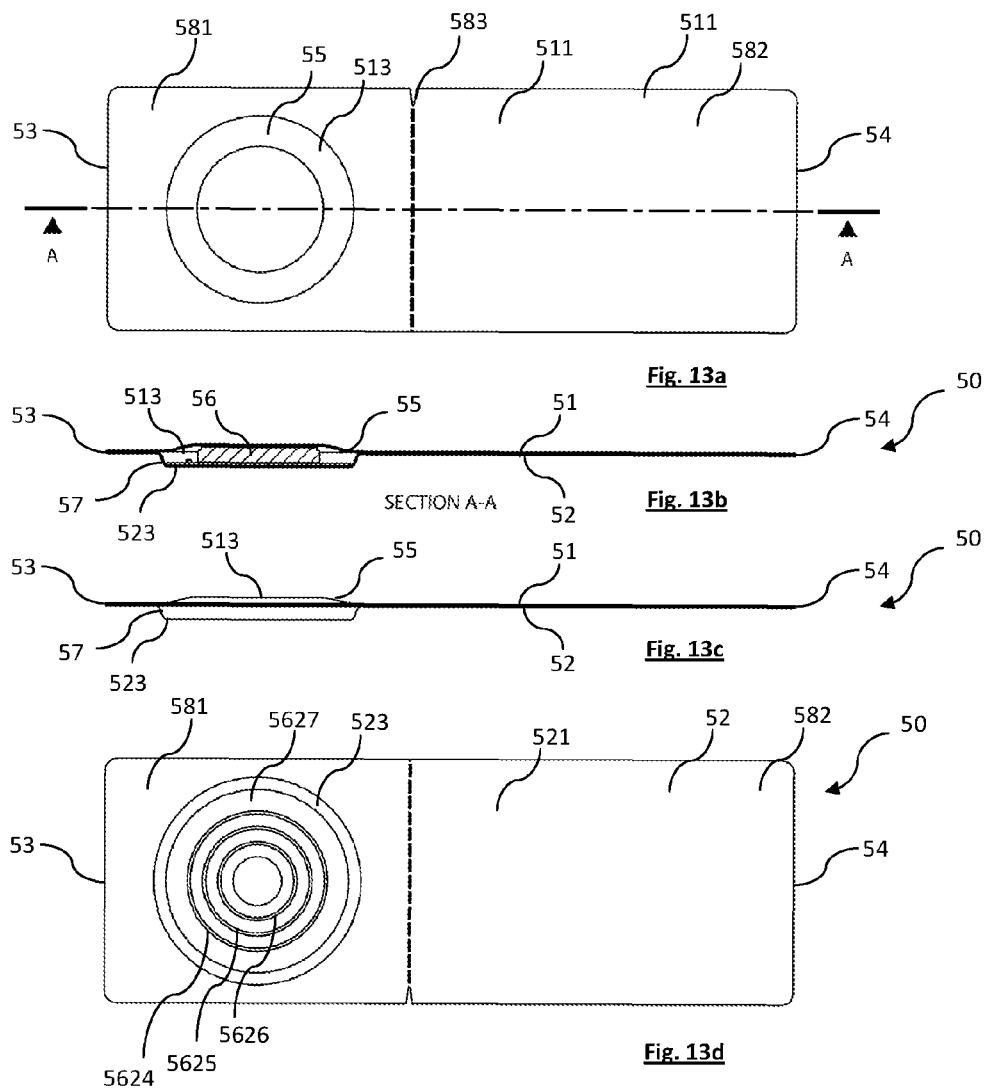

In combination, the relief 523 of the rear panel 52 and the outer surface 5627 of the PCB 562 can be considered to provide an engagement portion of the label 50, indicated in FIGS. 13b and 13c by reference numeral 57.

When the electronics unit 56 is securely held within the housing 55, the electronics unit 56 is sandwiched between inner surfaces of the reliefs 513, 523, whereupon the outer surface 5627 of the PCB 562 abuts against the rim 525, leaving a substantial portion of the outer surface 5627 of the PCB 562, including the first, second and third circular contacts 5624, 5625, 5626 exposed through the opening 524.

The base station 40 includes a front surface 41, and a plurality of receiving portions, in particular recesses 42, provided on the front surface 41. Each recess 42 is adapted to receive the engagement portion 57 of a respective label 50 by virtue of a frictional fit, as can be seen in FIG. 11b, for example. By providing a plurality of the recesses 42, the base station 40 can receive multiple labels 50 at the same time, each label being associated with a different medical device or different features of the same medical device. FIG. 11a includes a magnified view of one of the recesses 42. Each recess 42 has a bottom surface 420 with a plurality of electrical contacts 421a-423b projecting from the bottom surface 420. Upon receipt of an engagement portion 57 of a label 50 by a recess 42, two of the projecting electrical contacts 421a, 421b are adapted to connect with the first circular contact 5624, another two of the projecting electrical contacts 422a, 422b are adapted to connect with the second circular contact 5625, and another two of the projecting electrical contacts 423a, 423b are adapted to connect with the third circular contact 5626. These connections establish a power circuit between the base station 40 and the battery 561 of the label 50, and establish a resistance measurement circuit between the base station 40 and the label 50.

Figure 16:
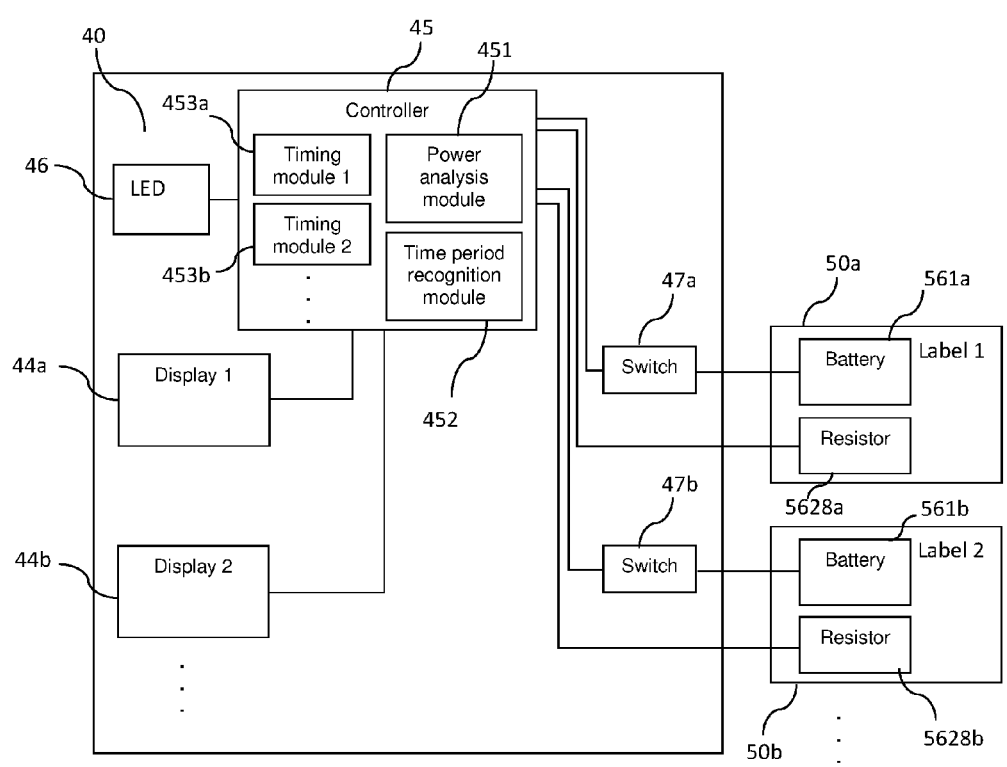

A schematic illustration of various electrical components of the monitoring system 4, including the base station 40 and labels 50a, 50b received by the base station 40, is provided in FIG. 16. For simplicity, FIG. 16 shows only two labels 50a, 50b and two displays 44a, 44b (each display 44a, 44b being for use with a respective one of the labels 50a, 50b). In practice, to the extent that the base station 40 is adapted to receive a different number of labels (e.g., adapted to receive five labels, as represented in FIG. 11a) a corresponding number of displays would be present. Substantially the same principles of operation of the system 4 can apply, regardless of the number of the plurality of labels.

The base station 40 comprises a controller 45 (e.g., a microcontroller) that is connected to each one of the displays 44a, 44b and to an LED 46. The controller controls the visual output of the displays 44a, 44b and illumination of the LED 46. When each label 50a, 50b is received by the base station 40, a respective power circuit is established between the controller 45 and the battery of the label 50a, 50b, which power circuit can be turned on and off by the controller using a switch 47a, 47b (e.g., a MOSFET). The controller 45 recognises the receipt of a label 50a, 50b based on establishment of the power circuit with the label 50a, 50b.

Upon establishment of the power circuit with the label 50a, 50b, the controller 45 determines a predetermined time period that is to be monitored in relation to the label 50a, 50b and more particularly the medical device associated with that label. Each label 50a, 50b provides information to the controller 45 about the predetermined time period using its resistor 5628a, 5628b. The controller 45 includes a time period recognition module 452, which measures the resistance of the resistor 5628a, 5628b (e.g., by virtue of a voltage drop measurement) using the resistance measurement circuit established between the base station 40 and the label 50a, 50b. The time period recognition module 452 determines the predetermined time period based on the measured resistance. In this embodiment, the time period recognition module 452 is adapted to recognise that a measured resistance falling within a first resistance range is indicative of a first predetermined time period (e.g., 24 hours), a measured resistance falling within a second resistance range is indicative of a second predetermined time period (e.g., 48 hours), a measured resistance falling within a third resistance range is indicative of a third predetermined time period (e.g., 72 hours), and measured resistance falling within a fourth resistance range is indicative of a fourth predetermined time period (e.g., 7 days). In general, however, there is no limit to the number of predetermined time periods that the base station may be configured to recognise based on different resistance measurements. Further, different predetermined time periods can be any appropriate predetermined time periods.

The controller includes a plurality of timing modules 453a, 453b, which are each associated with a respective one of the received labels 50a, 50b. Once the predetermined time period for a received label 50a, 50b is identified by the time period recognition module 452, the controller 45 inputs the predetermined time period to the associated timing module 454a, 454b. The timing module then counts down the predetermined time period. The countdown may start substantially immediately on receipt of the label 50a, 50b by the base station 40, after a pre-set delay, or upon receipt of a user input (e.g., upon pressing by the user of a button that is optionally included in the base station 40).

The controller 45 controls each display 44a, 44b to display the countdown of the predetermined time period for the label 50a, 50b associated with that display. This provides the user with a visual indication of the time left to expiry of the predetermined time period. Upon expiry of the predetermined time period, the controller 45 is adapted to cause the display 44a, 44b to flash (e.g., flash a zero time display "0:00:00" and/or a word such as "FINISHED") and cause the LED 46 to flash. While the same LED 46 is used in relation to multiple received labels 50a, 50b in this embodiment, the LED 46 may still draw a user's attention to the fact that a predetermined time period has expired in relation to at least one of the received labels 50a, 50b. The user may then observe which display(s) 44a, 44b is flashing, and thus identify the label(s) in relation to which a predetermined time period has expired.

Upon recognition that a predetermined time period relating to a label 50a, 50b has expired, the user may take a particular action in relation to the medical device that is associated with the label 50a, 50b. For example, if the medical device is a catheter, the user may remove and optionally replace the catheter. Once the predetermined time period has expired for a particular label 50a, 50b, that user can remove the label 50a, 50b from the base station 40. The second portion 582 of the label, which may include details of the associated medical device as discussed above, can be separated from the first portion 581 and placed in medical records of a patient. The second portion 582 may have an adhesive portion to enable attachment to medical records.

In this embodiment, when the base station 40 is in receipt of multiple labels 50a, 50b at the same time, the battery 561a, 561b of only one of the received labels 50a, 50b is used to power components of the system 4, including the controller 45, displays 44a, 44b and LED 46. To determine which battery 561a, 561b of the multiple labels 50a, 50b to use to power the components, the controller 45 includes a power analysis module 451, which scores (ranks) each battery 561a, 561b, based on a determination of the battery voltage (indicative of the energy remaining in the battery) and a determination of the remaining time left of the predetermined time period that is being monitored in relation to the label 50a, 50b associated with the battery 561a, 561b. The battery 561a, 561b offering the best combination of high battery voltage and shortest remaining time is selected, and the power circuit associated with the selected battery is turned on using the associated switch 47a, 47b. The approach ensures that, even if a label is unexpectedly removed from the base station 40 at any point in time, the system 4 will still have access to sufficient power from other batteries 561a, 561b to continue to monitor predetermined time periods.

Generally, it will be recognised that a controller used in conjunction with a monitoring system according to an embodiment of the present disclosure can comprise a number of control or processing modules for controlling one or more components of the system and may also include one or more storage elements, for storing data such as predetermined time period data. The modules and storage elements can be implemented using one or more processing devices and one or more data storage units, which modules and/or storage devices may be at one location (e.g., in a base station as shown in FIG. 16) or distributed across multiple locations (e.g., in both a base station and label) and interconnected by one or more communication links.

The modules can be implemented by a computer program or program code comprising program instructions. The computer program instructions can include source code, object code, machine code or any other stored data that is operable to cause the controller to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g., RAM) and/or non-volatile (e.g., ROM, disk) memory or otherwise.

Figure 17:
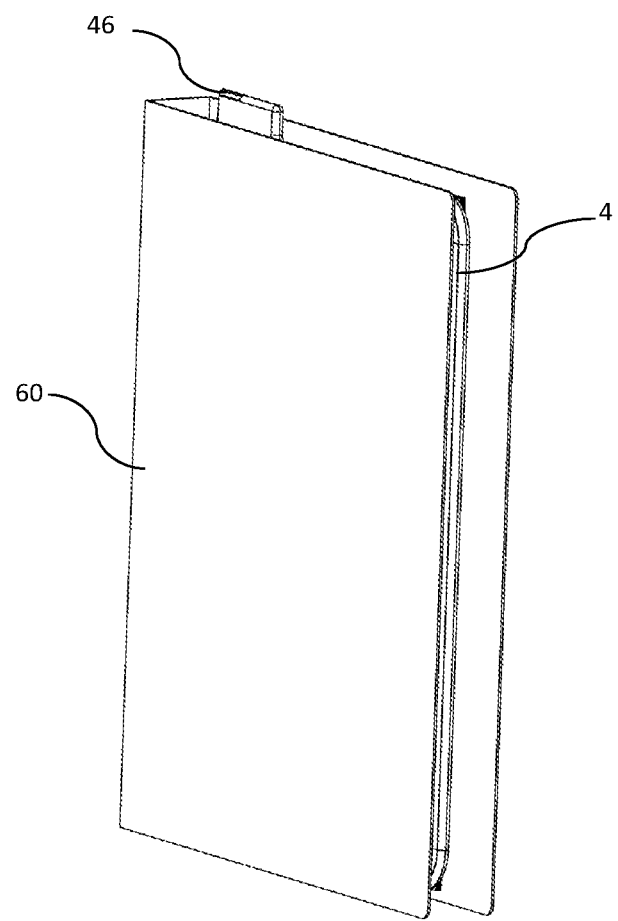
FIG. 17 shows an oblique view of the monitoring system of FIG. 11a held in the patient records holder while the patient records holder is in a closed configuration.

In the embodiment illustrated in FIG. 11a, the LED 46 is located at a top corner of the base station 40. The arrangement is such that, when the monitoring system, 4 including the base station 40 is held in the ring binder 60, and the ring binder 60 is closed as shown in FIG. 17, the LED 46 projects outwardly from the ring binder 60 and therefore remains visible to the user.

The ring binder 60 provides a form of patient or medical records holder. By configuring the monitoring system 4 for location within a records holder, the monitoring system 4 may be readily accessible by the user (e.g., a nurse, doctor or clinician, etc.), and held in a secure location at least during the duration of monitoring of the predetermined time period(s). In general, a medical records holder will remain in relatively close proximity to the patient at all times (usually at the end of the patient's bed, outside their room or at a nurses' station), and it is there readily and regularly accessible by medical staff. Fundamentally, the medical record is a source of status information relating to the patient, and therefore an ideal location for the monitoring system.

It will be appreciated by persons skilled in the art that numerous variations and/or modifications may be made to above-described embodiments, without departing from the broad general scope of the present disclosure.

For example, while, in the main embodiment of the monitoring system 4 described above, the base station 40 is adapted to identify a predetermined time period based on a resistance measurement, a variety of different approaches to identifying the predetermined time period may be employed, such as by communication of a coded signal from a chip that may be include in the label to the base station, or via an optical signal, a wireless signal, and/or by a shape or configuration of the label or otherwise. Alternatively, the base station may be pre-configured to monitor a single predetermined time period only.

As another example, while, in the main embodiment of the monitoring system 4 described above, the base station 40 is adapted to receive multiple labels, in alternative embodiments the base station may be adapted to receive a single label only. It may therefore include only one receiving portion to engage with a label.

As yet another example, while, in the main embodiment of the monitoring system 4 described above, the system is powered by a battery in a label, in alternative embodiments the base station may include a battery or other power source (e.g., a mains power connection) to at least partly power the monitoring system.

As yet another example, while, in the main embodiment of the monitoring system 4 described above, the system is adapted to locate in a ring binder, the monitoring system in this or alternative embodiments may be configured to locate in other types of holders, such as a wall-mounted holder or a desk-mounted holder. In some healthcare environments, it is known to write patient records (or patient data) on a whiteboard. The monitoring system may be locatable in a holder that is mounted on or adjacent to a whiteboard.

The present embodiments are, therefore, to be considered in all respects as illustrative and not restrictive.

The invention claimed is:

1. A label comprising:
   a first portion and a second portion, the first and second portions being connected together;
   wherein the first portion comprises a timer to monitor a predetermined time period, a signalling apparatus that provides an alert signal on expiry of the predetermined time period, and a power source to supply power to the timer and signalling apparatus;
   wherein an adhesive is provided on a rear surface of the second portion to fix the label to a support surface during monitoring of the predetermined time period; and
   wherein at least one of a frangible element, a tear line, a tear notch, perforations and a region of weakness is located between the first portion and the second portion to enable disconnection of the first portion from the second portion when the second portion is fixed to the support surface by the adhesive and after monitoring of the predetermined time period.

2. The label of claim 1, wherein the support surface is provided by patient medical records.

3. The label of claim 2, wherein the medical records comprise one or more sheet elements of paper, plastic or card.

4. The label of claim 2, wherein the first portion is arranged to overhang an edge of the medical records when the label is fixed to the medical records by the adhesive.

5. The label of claim 1, wherein the support surface is provided by a surface of a container.

6. The label of claim 1, wherein the second portion is planar.

7. The label of claim 1, wherein the label is a single-use label.

8. The label of claim 1, wherein the second portion comprises a display portion, including a surface on which a user can write information and/or a surface on which information is pre-printed.

9. The label of claim 1, wherein the signalling apparatus provides a first type of alert signal prior to expiry of the predetermined time period and a second type of alert signal upon expiry of the predetermined time period, the first and second types of alert signal being different.

10. The label of claim 9, wherein the first type of alert signal is emitted upon an actuation step being carried out by a user.

11. The label of claim 10, wherein the actuation step comprises pressing a button comprised in the label.

12. The label of claim 1, wherein the label comprises a tab that is removable to initiate monitoring of the predetermined time period by the timer.

13. The label of claim 1, wherein the adhesive is covered by a removable backing layer.

14. The label of claim 13, wherein removal of the backing layer initiates monitoring of the predetermined time period.

15. Medical records comprising the label according to claim 1.

16. A container comprising the label according to claim 1.

17. The label of claim 1, wherein the label has a longitudinal axis and the first and second portions of the label are located opposite to each other along the longitudinal axis.

18. The label of claim 1, wherein the timer is provided by a processor and wherein the signalling apparatus comprises an LED and the power source comprises a battery.

19. The label of claim 1, wherein adhesive is not provided on a rear surface of the first portion of the label.

20. The label of claim 1, wherein the second portion of the label does not comprise any electronic components.

* * * * *